US011213244B2

(12) United States Patent
Vardy

(10) Patent No.: US 11,213,244 B2
(45) Date of Patent: *Jan. 4, 2022

(54) COLLECTION OF MEDICAL DATA

(71) Applicant: IsoTechnology Pty Ltd, Queensland (AU)

(72) Inventor: Terence Vardy, Tweed Heads (AU)

(73) Assignee: IsoTechnology Pty Ltd, Burleigh Waters (AU)

(*) Notice: Subject to any disclaimer, the term of this patent is extended or adjusted under 35 U.S.C. 154(b) by 94 days.

This patent is subject to a terminal disclaimer.

(21) Appl. No.: 16/048,572

(22) Filed: Jul. 30, 2018

(65) Prior Publication Data

US 2019/0059801 A1    Feb. 28, 2019

Related U.S. Application Data

(63) Continuation of application No. 14/769,077, filed as application No. PCT/AU2014/000149 on Feb. 20, 2014, now Pat. No. 10,034,632.

(30) Foreign Application Priority Data

Feb. 20, 2013    (AU) .................... 2013200948

(51) Int. Cl.
*A61B 5/00*    (2006.01)
*A61B 5/22*    (2006.01)
*G16H 10/60*   (2018.01)
*G16Z 99/00*   (2019.01)
(Continued)

(52) U.S. Cl.
CPC ............ *A61B 5/4023* (2013.01); *A61B 3/113* (2013.01); *A61B 5/0022* (2013.01);
(Continued)

(58) Field of Classification Search
CPC ..... A61B 5/4023; A61B 5/225; A61B 5/1036; A61B 5/1125; A61B 5/0077; A61B 3/113;
(Continued)

(56) References Cited

U.S. PATENT DOCUMENTS 5,987,982 A     11/1999  Wenman et al. .......... 73/379.08
6,903,723 B1 *   6/2005  Forest ...................... A61F 4/00
                                                        345/157
(Continued)

FOREIGN PATENT DOCUMENTS

AU       2013200948 A1     3/2013
WO    WO 2006/100675 A2    9/2006
WO    WO-2006100675 A2 *   9/2006  ............. G16H 10/20

OTHER PUBLICATIONS

Non-Final Office Action dated Mar. 16, 2017 of corresponding U.S. Appl. No. 14/769,077.

(Continued)

*Primary Examiner* — Catherine M Voorhees
(74) *Attorney, Agent, or Firm* — Bradley Arant Boult Cummings LLP

(57) ABSTRACT

A system and method for assessing a patient's balancing ability in order to facilitate ascertaining the patient's current medical status. The system includes a balance plate for measuring the meter of gravity dynamic weight distribution in combination with a sensor for measuring the patient's fine motor skills.

22 Claims, 23 Drawing Sheets

(51) Int. Cl.
*G16H 10/65* (2018.01)
*G16H 40/63* (2018.01)
*A61B 3/113* (2006.01)
*A61B 5/103* (2006.01)
*G16H 50/20* (2018.01)
*G16H 15/00* (2018.01)
*A61B 5/377* (2021.01)
*A61B 5/11* (2006.01)

(52) U.S. Cl.
CPC ............ *A61B 5/0077* (2013.01); *A61B 5/225* (2013.01); *G16H 10/60* (2018.01); *G16H 10/65* (2018.01); *G16H 40/63* (2018.01); *G16Z 99/00* (2019.02); *A61B 5/002* (2013.01); *A61B 5/0013* (2013.01); *A61B 5/1036* (2013.01); *A61B 5/1125* (2013.01); *A61B 5/1128* (2013.01); *A61B 5/377* (2021.01); *A61B 5/4064* (2013.01); *A61B 5/706* (2013.01); *A61B 2560/0475* (2013.01); *G16H 15/00* (2018.01); *G16H 50/20* (2018.01)

(58) Field of Classification Search
CPC .......... A61B 5/0022; A61B 2560/0475; A61B 5/706; A61B 5/4064; A61B 5/1128; A61B 5/002; A61B 5/0013; A61B 5/0484; G16H 10/60; G16H 50/20; G16H 15/00; G16Z 99/00; G06F 19/00; G06Q 50/22; Y02A 90/22; Y02A 90/26
See application file for complete search history.

(56) References Cited

U.S. PATENT DOCUMENTS

| | | | | |
|---|---|---|---|---|
| 10,034,632 | B2* | 7/2018 | Vardy | .................... A61B 5/225 |
| 2005/0159674 | A1 | 7/2005 | Harbin et al. | ................ 600/558 |
| 2009/0144092 | A1* | 6/2009 | Vardy | .................... G06F 19/00 705/3 |
| 2011/0034784 | A1* | 2/2011 | David | .................. A61B 5/0205 600/301 |
| 2011/0160796 | A1* | 6/2011 | Lane | .................. A61N 1/36139 607/45 |
| 2011/0175736 | A1* | 7/2011 | Shieh | .................... G01G 19/50 340/573.1 |
| 2011/0251520 | A1* | 10/2011 | Shieh | .................... A61B 5/7275 600/587 |
| 2011/0256983 | A1 | 10/2011 | Malack et al. | .................... 482/4 |
| 2012/0235819 | A1* | 9/2012 | Watkins | .................. A61B 5/18 340/573.1 |
| 2013/0171600 | A1* | 7/2013 | Yuasa | .................... G09B 19/00 434/258 |
| 2014/0045656 | A1* | 2/2014 | Zhang | .................... G16H 20/30 482/4 |
| 2014/0272853 | A1 | 9/2014 | Sakai et al. | .................. 434/247 |

OTHER PUBLICATIONS

Final Office Action dated Sep. 8, 2017 of corresponding U.S. Appl. No. 14/769,077.
Final Office Action dated Dec. 19, 2017 of corresponding U.S. Appl. No. 14/769,077.
Notice of Allowance dated Apr. 2, 2018 of corresponding U.S. Appl. No. 14/769,077.
International Search Report and Written Opinion of the International Searching Authority dated Apr. 8, 2014.
Written Opinion of the International Preliminary Examining Authority dated Feb. 5, 2013.
International Preliminary Report on Patentability dated Jun. 12, 2015.
European Office Action dated Jan. 8, 2019 of corresponding European Patent Application No. 14754441.5.

* cited by examiner

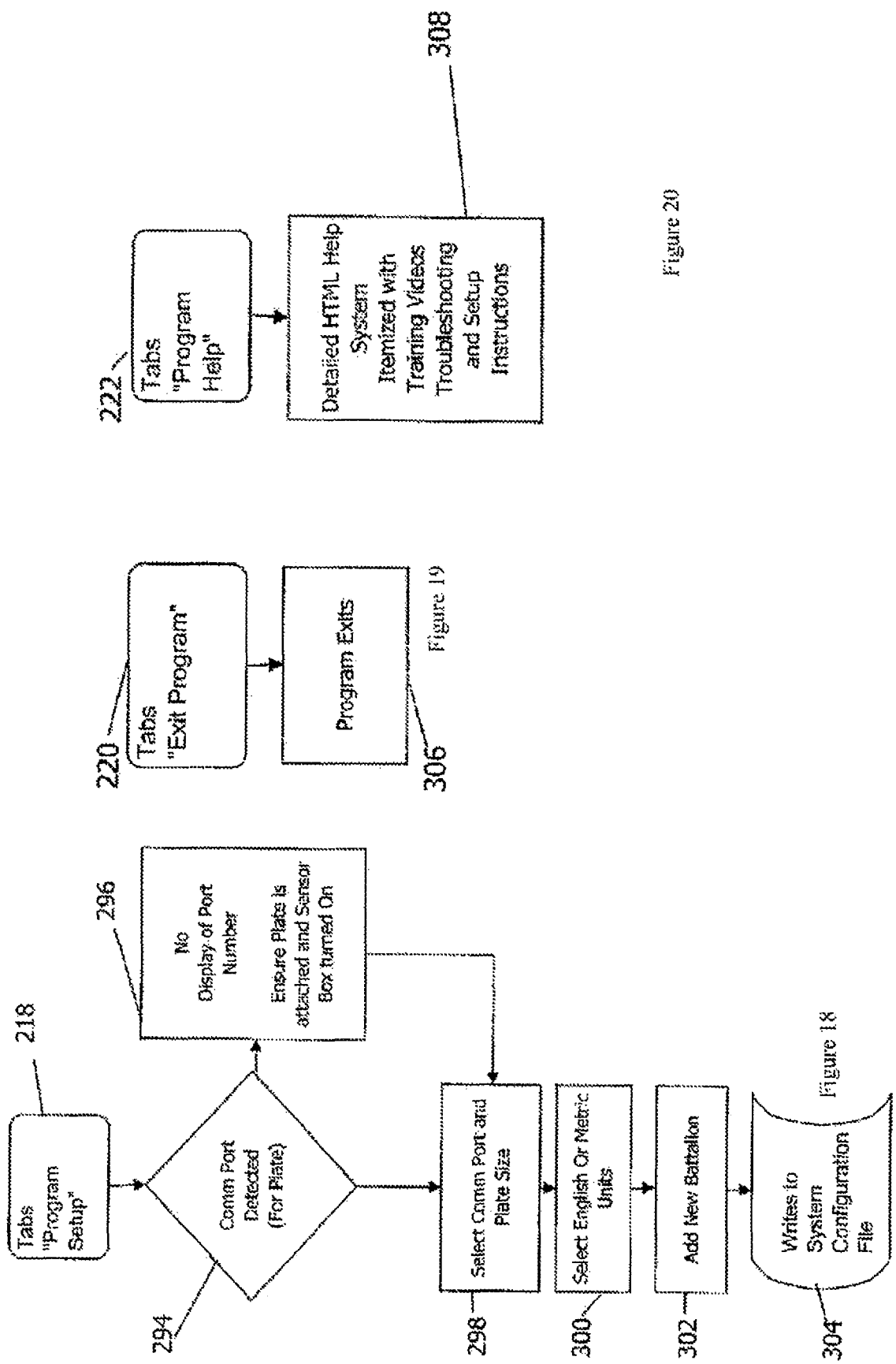

(A) Baseline testing
EC/Sit    EC/Stand    EC/Foam
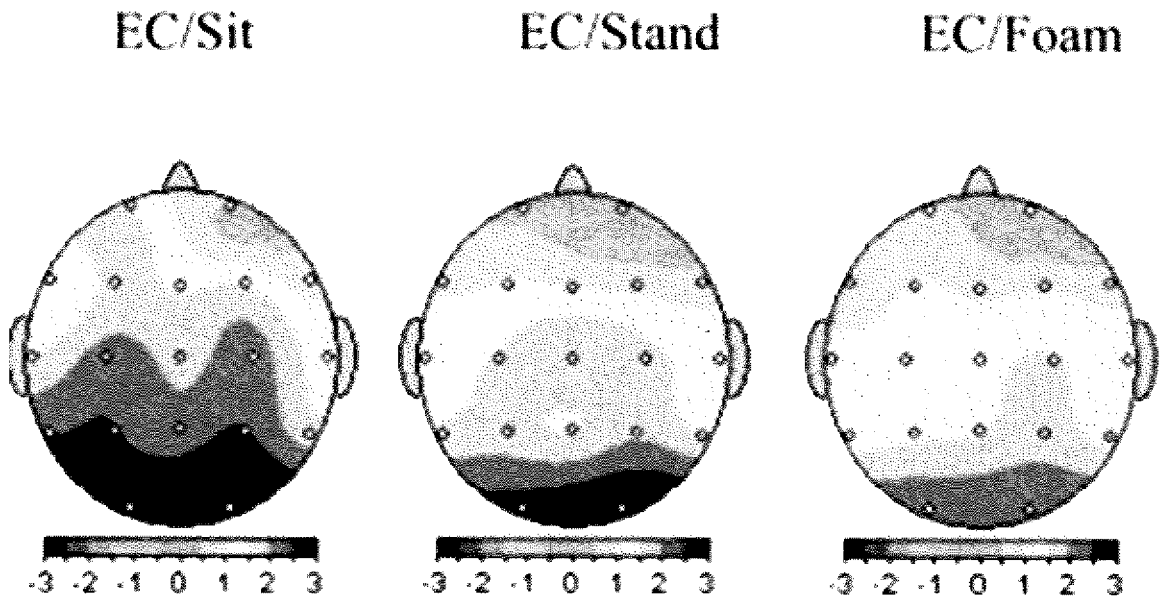
(B) 7 days post-MTBI
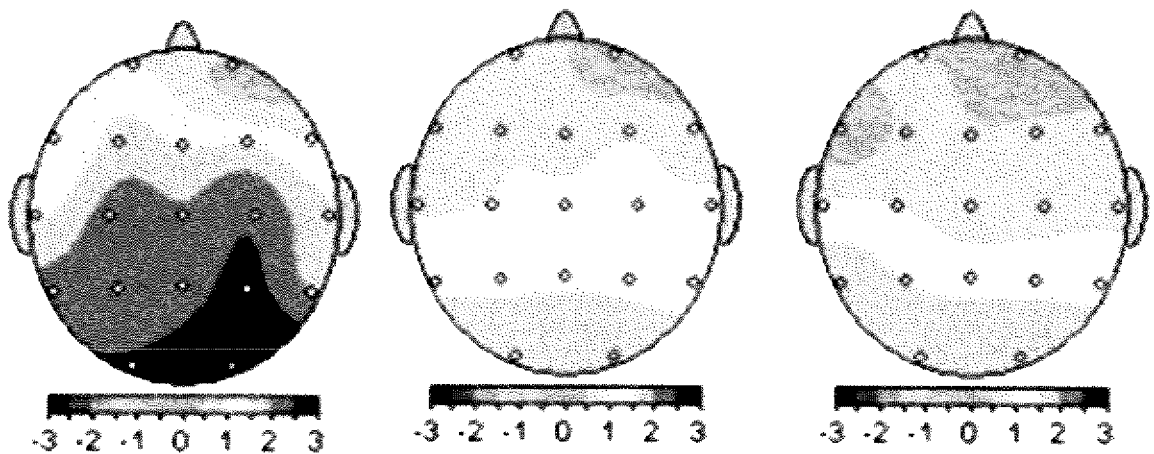
FIG. 25

COLLECTION OF MEDICAL DATA

FIELD OF THE INVENTION

This invention relates to the collection of medical data. In particular, the invention relates to a system, a method and a software product for collecting medical data.

The present invention has been developed primarily for use in the medical, health and fitness industries and will therefore be described in that context. It is to be appreciated, however, that the database may have other uses, including collection of visual images at accident sites and crime sites.

BACKGROUND ART

In the medical and fitness industries, data about individual patients is increasingly being recorded electronically in computer databases rather than in paper files. The reason is that electronic records can be generated, stored and retrieved more readily than paper files.

However, a disadvantage with presently available data collection systems and methods is that they are not able properly to generate reports containing different types of data. For example, it can be desirable that the reports include images of an injury or an incident location where the patient is an accident or crime victim.

SUMMARY OF THE INVENTION

According to a first aspect of the invention, there is provided a system for collecting medical data, the system comprising
a database server programmed to receive data in a number of different formats from respective different data sources, the database server being connectable to a communications network; and
a number of remote data collection arrangements associated with respective medical operators and equipment and each configured to permit said respective medical operators to input medical data relating to a medical condition of a patient into the data collection arrangement and to write the medical data to the database server via the communications network, the database server being configured to receive the medical data and to generate an electronic record representing a compilation of different items of the medical data.

The database server may be connectable to the communications network via a web server, the communications network being in the form of the Internet.

The remote data collection arrangements may include data processors with respective memories for storing the medical data. The memories of the remote data collection arrangements may include a removable data storage device that is compatible with other data processors in the system, to enable additional medical data to be input into the removable data storage device as a patient is moved from one treatment point to another.

The remote data collection arrangements may include personal digital assistants (PDAs) configured to record images and text input for transmittal to the database server. The remote data collection arrangements may also include medical devices configured to record physiological characteristics of a patient.

The remote data collection arrangements may be configured to permit the recording of speech. For example, the PDAs may be of the type suitable for speech recording. Instead, the remote data collection arrangements may include dictation systems equipped with a headset and appropriate software to allow the dictation of notes.

According to a second aspect of the invention, there is provided a method for collecting medical data, the method comprising the steps of:
inputting data relating to a medical condition of a patient to a remote data collection arrangement at an incident location;
storing the data in a removable data storage device at the incident location;
transferring the patient to at least one intermediate treatment location together with the removable data storage device;
inputting further data relating to the medical condition of the patient to a further data collection arrangement at the at least one further intermediate treatment location;
storing the further data in the removable data storage device;
transferring the patient to a final treatment location together with the removable storage device; and
compiling an electronic record relating to the medical condition of the patient from the data.

According to a third aspect of the invention, there is provided a method for collecting medical data, the method comprising the steps of:
inputting medical data relating to a medical condition of a patient to at least one remote data collection arrangement;
writing the medical data to a database server via a communications network; and
compiling the medical data to generate an electronic record of the medical condition of the patient.

The steps of inputting and writing the medical data may be carried out with respect to the same patient at an incident location and, thereafter, at least one further treatment location.

The steps of inputting and writing the medical data at the incident location may be carried out with a personal communications device, such as a personal digital assistant (PDA) capable of capturing both image and text data.

According to a fourth aspect of the invention, there is provided a software product which is configured so that, when executed by a data processing device, is configured to carry out a method comprising the following steps:
establishing a communications link between the data processing device and a data collection arrangement at an incident location;
generating an interface on the remote data collection arrangement to facilitate the input of medical data relating to a medical condition of a patient at the incident location;
associating the medical data with sensor data captured at the incident location;
writing the medical and sensor data to a database stored in the data processing device; and
generating an electronic record from the database containing the medical and sensor data.

The software product may be configured so that the medical data and the sensor data can be associated with each other on the data processing device. The medical data can be associated with the sensor data in the form of at least one of: still image data, video data, sound data, and analytical data from a connected analytical device.

The software product may be configured so that, when executed, the data processing device generates the database in the form of a relational database with the medical and sensor data.

The software product may be configured so that, when executed, the data processing device generates the interface in the form of a graphic user interface (GUI) that defines fields for inputting the medical data.

The invention extends to a data processing device when programmed with a software product as described above.

The software product may be configured so that, when executed, there is provided a database capable of:

generating an electronic record about a person or an event;

storing said record;

retrieving and transmitting said record;

enabling a user to input data about said person or event, and incorporating the data into said record;

capturing sensor data relating to said person or event, and incorporating the sensor data into said record; and analysing the data and incorporating an analysis of the data into said record.

The software product may further be configured so that there is provided a database capable of generating, storing, retrieving and transmitting an electronic record about a person or an event, said database comprising a least one electronic record about a person or event, wherein said record:

incorporates data about said person or event that has been inputted by a user;

incorporates captured sensor data relating to said person or event; and incorporates an analysis of the data.

The database may be used in the medical and fitness industries, in which case the electronic record could contain data relating to a person's medical and performance history. Alternatively, the database may be used in the racing industry, and the electronic record could contain data relating to a race horse's or greyhound's medical and performance history. Alternatively, the database may be used to contain data from an event, such as forensic data from a crime scene, and the electronic record could contain data relating to the crime scene and analyses of the crime scene as conducted by forensic scientists.

Preferably, the database is used in the medical and fitness industries by medical practitioners or therapists, and contains records of people's medical and performance history.

The software product may be configured so that the database enables the user to input data about a person or event in any suitable way. Likewise, the inputted data may be incorporated into the record in any suitable way. Typically, the software product is capable of generating GUIs that include one or more fields for inputting data relating to one or more of the following: the person's name, address, date of birth, sex, height, weight, occupation, family medical history, medical history and symptoms, and current medications. The number and types of fields will depend on what data needs to be recorded.

The sensor data relating to the person or event can be captured and incorporated into the record in any suitable way. The sensor data may be of any suitable nature. The sensor data may be, for example, in the form of a still image (e.g. captured from a digital still camera, digital video camera, or a cell phone), a moving image (e.g. captured from a video camera) or a sound recording (e.g. captured from a digital dictaphone). Alternatively, the sensor data may be captured from a connected measurement instrument, such as a balance system, CT scan, MRI, or ultrasound machine. The sensor data may be transmitted to the database via a cable or wireless connection.

The user inputted data and sensor data may be analysed and incorporated into the record in any suitable way. The captured still image may be, for example, of a person's wound or posture. Analyses and measurement may be made of the size of the wound, or posture.

The moving image may be, for example, of a person and analyses may be made of the person's gait, joint flexibility or body shifts during certain activities. Alternatively, analyses may be made of the person's strength, agility, speed, flexibility or other abilities. The analysis may be conducted manually by the user or automatically by a function or algorithm of the software product.

The balance system may utilize a plurality of force plates and/or load cells to measure a person's balance over a period of time. Preferably, the person's balance is measured in two 15-60 second intervals—with their eyes open during the first interval and with their eyes closed during the second interval. The balance data can provide information on numerous conditions including neurological disorders, dysfunctional posture, comparative range of motion, and balance status of aged care or injured patients.

User inputted data and/or sensor data from more than one source may be captured and combined for analysis. For example, video data and balance system data may be captured simultaneously.

The record preferably provides historical comparisons so as to indicate the person's progress, to allow actual progress to be compared against their goals, and to allow the user to fine-tune treatment of the person.

Electronic records about persons or events may be generated, stored, retrieved and transmitted in any suitable way. Any suitable type of programming language may be used. Preferably, the data is encrypted and stored in a relational schema, and the record is transmitted using electronic communication; for example, via email, computer networks, the internet, cellular networks, discs (e.g. CD's, DVD's), or using USB connected flash memory drives and physically transporting the records. The use of USB connected flash memory drives is preferable for situations where the data is confidential but not time-sensitive, as it is slow to transfer but improves the security of the data and makes it considerably more difficult for unauthorised parties to access the data. Additionally, the data may be committed to a paper record.

Electronic records may be transmitted to authorised parties, such as medical practitioners, therapists, administrators and insurance companies. In some cases, the data may be subjected to further analyses by some of the authorised parties and the record may be further updated. Different authorised parties may have different levels of authorisation, determining on which portions of the data they have been authorised to view.

The preferred balance system embodiment can be used as one portion of a multifactor testing or monitoring system. Preferably, that embodiment can be used in conjunction with one or more additional assessment modules including at least one module directed toward using sensory input to assess fine motor control, a cognition assessment module, an event related potential assessment module, eye tracking module, fine motor control assessment module, an entropy values calculation module adapted to utilise data collected through a balance assessment for example, a sway velocity module to utilise data collected through a balance assessment for example and other physiological assessment modules such as a electroencephalogram. The data collected or characterising data calculated by any one of the assessment modules can be utilised by any of the other assessment modules or data from one module can be analysed in conjunction with the data from any other module to provide a more robust clinical tool.

One preferred form of cognition assessment is a software product including a set of tests designed to test the subject's ability to determine, memorize and recall the pattern of two (2) symbols. 'Arrow' keys are used on the keyboard—Right & Left—to choose the specific symbol. A preferred first task is to determine a pattern—two distinct shapes will be shown. The subject preferably uses the left or right arrow keys on a keyboard, or touches the appropriate location on the touch-pad or smart-phone to make a selection. The system will display if the subject has selected the correct symbol or not. A preferred second task is to recall the set of patterns discovered in step one. The response times and selections are preferably evaluated and displayed in a graphed format and in a comparative display weighted against a database average.

An Event Related Potentials (ERP) assessment tool can be used for detailed analysis of the ERP's against a normative database to detect abnormalities and map behavioural parameters and improvement. An event-related potential (ERP) is the measured brain response that is the direct result of a specific sensory, cognitive, or motor event.

More formally, it is any stereotyped electrophysiological response to a stimulus. The study of the brain in this way provides a non-invasive means of evaluating brain functioning in patients with cognitive diseases.

ERP component abnormalities in clinical research have been shown in neurological conditions such as:
Dementia
Parkinson's disease
Multiple sclerosis
Head injuries (MTBI)
Stroke An "Eye Tracking" system to measure and analyze eye movements can be incorporated in the balance system. This additional measurement would show comparative eye movements in real time with balance changes.

A handgrip sensor could be attached to the system using a USB cable or wireless/Bluetooth connection. This addition would enable the screening of grip strength and initial and ongoing evaluation of subjects with fine motor skills impairment.

A preferred construction is a strong aluminum body construction with scratch resistant UV coating. The readout preferably displays isometric grip force from 0-200 lbs. (90 kg.). The unit is typically provided with an easy-to-read LCD display that can be set to display pounds or kilograms. An integrated dynamometer also features digital load cell technology. This tool preferably allows rapid exchange testing with audible signals. The output will normally include the average, standard deviation, and coefficient of variation of a number of different tests and allows comparison with a database collection.

Entropy values can be calculated on physiological or other data collected throughout one or more balance tests. Theoretical entropy is a measure of the order or disorder, and in this case gives an additional measure to the predictability and diversity of the test subject's activity. Preferably, both Shannon and Renyi Entropy values are produced.

Shannon entropy is static measure of entropy. Renyi entropy represents a scalable calculation based around the Shannon entropy. The Renyi entropy used in the system has been given a parameter of 2 (which represents a measure known as the "collision entropy").

Entropy calculations are typically performed using the following procedure.
1. Normalize COG (Center of Gravity) data; using the mean COG point and the standard variation of that data;
2. Cluster the data into segments so the COG points overlap and produce meaningful probabilities (e.g. split the grid into 100 brackets and round the values into the nearest bracket);
3. Calculate the entropy (Shannon or Renyi);
4. Normalize the resulting entropy into the range of 0.0 to 1.0.

Sway velocity can be calculated based on a subject's test results and the calculations saved and used in a pattern matching query to isolate groups or anomalous test results.

Average sway velocity is determined by calculating the sum of the COP displacements in the AP-ML plane over a trial (i e, the sway path length) and dividing this number by the recording time, i.e., 30 seconds.

EEG in conjunction with Balance can be used as a robust clinical tool for assessment of mild traumatic brain injury (MTBI).

The system allows for a concussion assessment protocol combining a series of EEG and balance measures throughout one year post injury to document recovery of patients suffering from MTBI. This allows for an establishment of an initial baseline of subjects prior to any exposure to MTBI.

The new Database system allows for the creation and editing of custom tests with durations from 30 seconds to 180 seconds. The custom tests can have different parameters and have an optional alert to indicate if the subject is within a certain parameter.

The database structure allows for all components to be modular and yet share a common database interface to allow for the easy export and import of the subject data and test results.

The cumulative database can be compiled individually in any one system, shared using the export function, or imported and used for comparative analysis of subject tests.

The addition of the balance sway velocity calculation will allow for advanced grouping of subject test results within the database and assist in detecting outliers and anomalous tests.

In order that the invention may be more readily understood and put into practice, one or more embodiments thereof will now be described, by way of example only, with reference to the accompanying figures.

BRIEF DESCRIPTION OF THE FIGURES

FIG. 18 shows a flowchart of steps carried out when a "Program Setup" tab generated by the software product is selected.

FIG. 19 shows a flowchart of steps carried out when an "Exit Program" tab generated by the software product is selected.

FIG. 20 shows a flowchart of steps carried out when a "Program Help" tab generated by the software product is selected.

FIG. 25 is a sample EEG output both at initial baseline and 7 days post mild traumatic brain injury showing activity.

DESCRIPTION OF PREFERRED EMBODIMENTS

Figure 1:
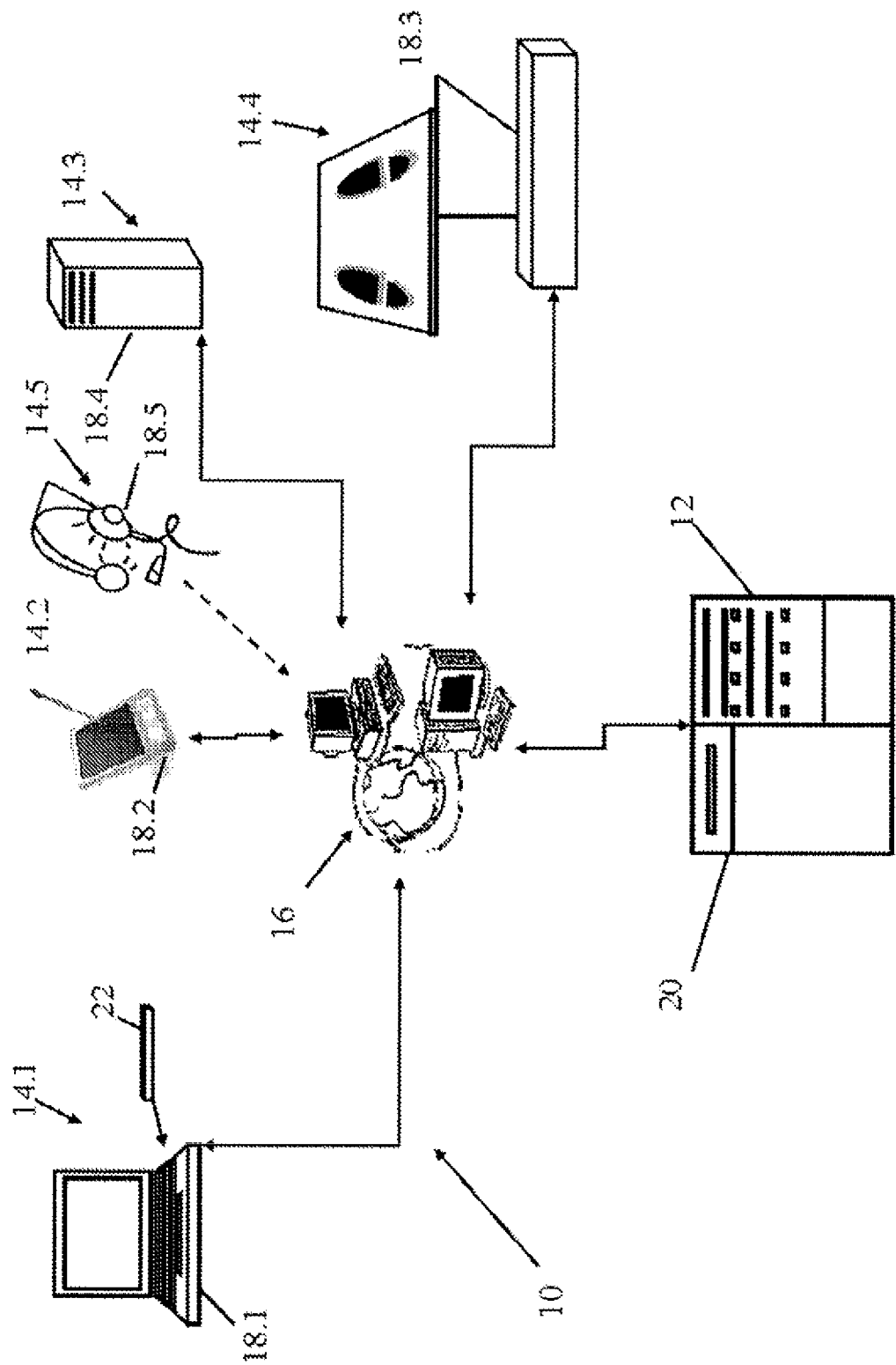
FIG. 1 shows an embodiment of a system, in accordance with the invention, for collecting medical data.

In FIG. 1, reference numeral 10 generally indicates an embodiment of a system, in accordance with the invention, for collecting medical data.

The system 10 includes a database server 12. The database server 12 is programmed to receive data in a number of different formats from respective different data sources 14.1 to 14.5, for example. The database server 12 is connected to a communications network, in this example, the Internet indicated at 16.

The different data sources 14 are generated by remote data collection arrangements, in the form of a laptop computer 18.1, a personal digital assistant (PDA) 18.2, a balance board and data processor arrangement 18.3, a headset 18.5 for recording and digitizing speech, and any other data collection arrangement 18.4 configured to permit a medical operator to input medical data relating to a medical condition of a patent into the data collection arrangement 18. Common to the data collection arrangements 18 is the ability to write the medical data to the database server 12 via the Internet 16, the database server 12 being configured to receive the medical data and to generate an electronic record representing a compilation of different items of the medical data.

The database server 12 is connected to the network with a web server 20.

The remote data collection arrangements 18 all include data processors with respective memories for storing the medical data. For example, the laptop 18.1 is provided with a removable memory device 22 capable of being removed and delivered to a treatment center together with the patient.

Figure 2:
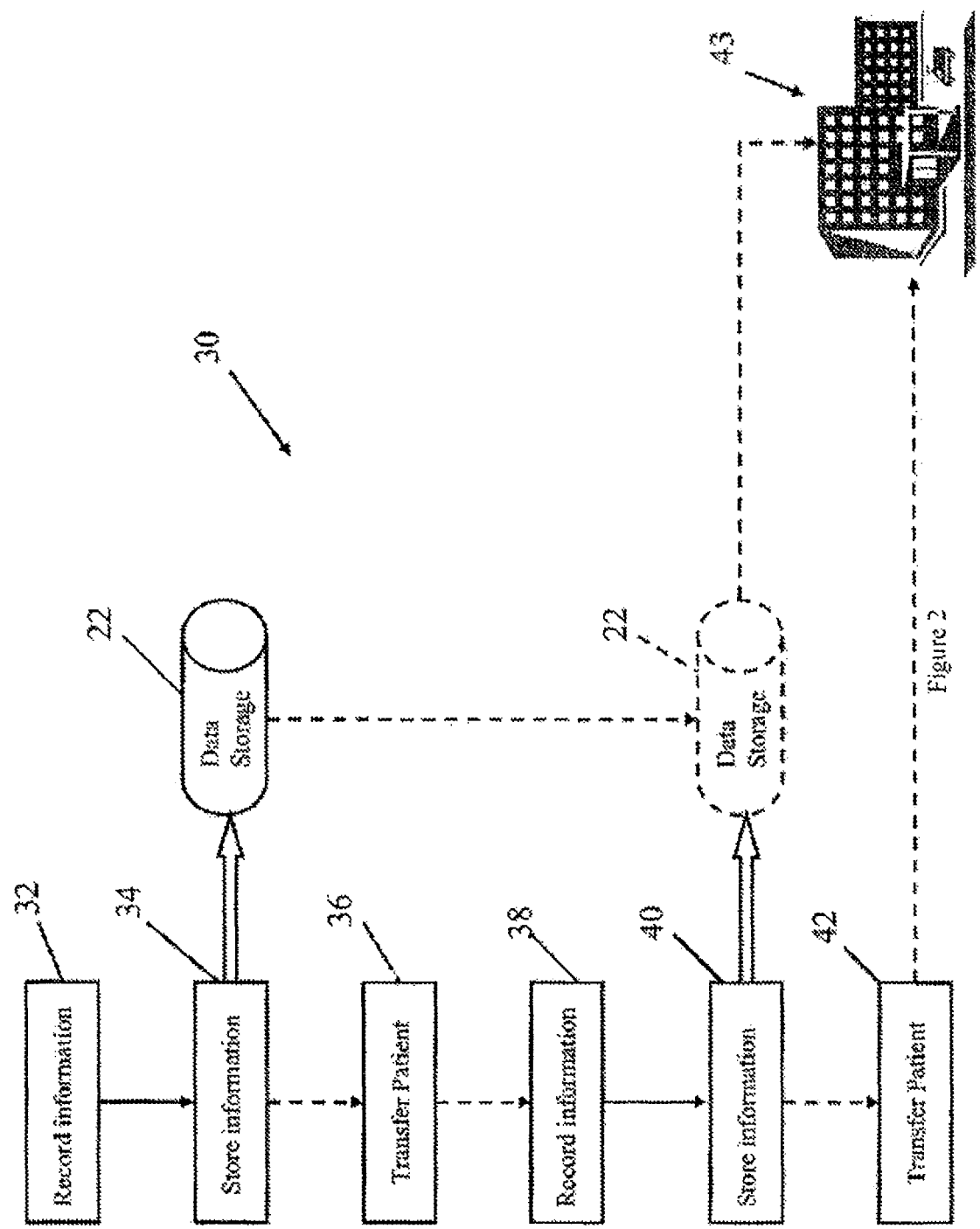
FIG. 2 shows an overview of an embodiment of a method, in accordance with the invention, for collecting medical data.

In FIG. 2, reference numeral 30 generally indicates a broad overview of a method, in accordance with the invention, for collecting medical data. In particular, the method 30 is configured for collecting medical data relating to an incident at an incident location and to collect further medical data at intermediate treatment locations prior to the patient arriving at a final treatment location.

Thus, at block 32, a medical operator records information on the removable memory device 22 at the incident location with the laptop 18.1. Instead, the medical operator could use the PDA 18.2 with the removable device 22 connected to the PDA.

The information is stored at block 34 and the patient is transferred at 36 together with the memory device 22 to an intermediate treatment location where further information is recorded at 38. The removable memory device 22 is programmed so that data stored at 32 cannot be over-written at 38. Furthermore, items of data recorded at 32 and 38 are tagged or associated with identification data, for example times, dates, medical operator identification and location to facilitate entry of that data into a suitable database, such as a relational database. At 40, the further information generated at 38 is stored and the memory device 22 is transferred at 42, together with a patient, to a final treatment location indicated at 43.

It will be appreciated that the information stored in the manner described above lends itself to the building of a database. In this example, a relational database is provided. However, it will be appreciated that other forms of database are also suitable.

Figure 3:
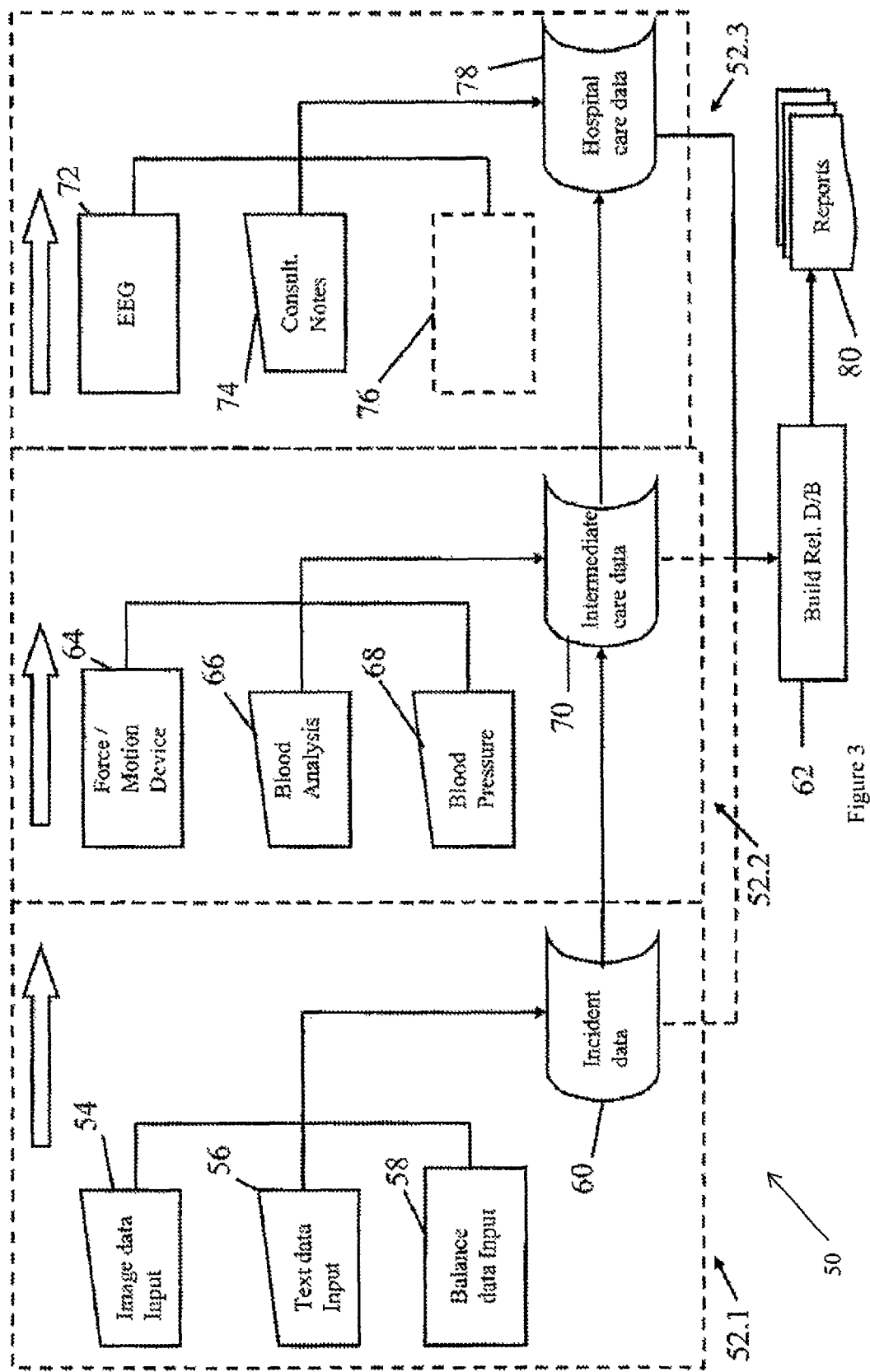
FIG. 3 shows steps carried out by an embodiment of a software product and a method, both in accordance with the invention, for collecting medical data.

In FIG. 3, reference numeral 50 generally indicates a flowchart that represents one embodiment of a method and a software product, both in accordance with the invention, for collecting medical data in the form of a relational database.

As can be seen in FIG. 3, the flowchart 50 is divided into three blocks 52. Each block 52 represents steps carried out at three separate locations. In particular, block 52.1 is an incident location where emergency care is carried out. Block 52.2 is an intermediate location where intermediate care is performed and 52.3 is a final treatment location where final care, such as hospital care is carried out.

Such an arrangement may occur, for example, in a military situation. Thus, 52.1 can represent a location where a soldier is injured and becomes a patient. At that location, a number of steps are carried out. These include recordal of image data at 54, for example photographic images of wounds, patient position and incident location. The recordal of the image data can be carried out with a personal digital assistant (PDA) that is programmed to permit a medical operator to enter text data (at 56) associated with the image and other medical notes related to the injury. The PDA can be programmed so that the medical operator can generate electronic images that overlie the photographic image, thereby allowing the medical operator to highlight wounds.

In this particular example, the medical operator can have access to a balance board to generate balance data to be input at 58. The three forms of data 54, 56, 58 make up incident data 60. The incident data 60 can be stored on the removable memory device 22 which is then sent, together with the patient, to the intermediate location 52.2, such as a battlefield clinic. Alternatively, the incident data 60 can be transmitted, in any suitable fashion, to the database server 12 to facilitate the building of a medical database at 62 by the software product.

At the intermediate location or battle field clinic 52.2, force/motion data can be input at 64 together with blood analysis data at 66 and blood pressure data at 68. It will readily be appreciated that other forms of electronic data can also be input at 52.2. These forms of data are collated as intermediate care data at 70. The intermediate care data 70 can be written to the device 22. As before, in an alternative embodiment, the intermediate data 70 can be communicated to the database server 12 to build the relational database at 62.

At the final treatment location, in this case a hospital 52.3, further data is recorded. For example, at 72, EEG data can be recorded. At 74, consultation notes can be electronically generated and, at 76, indicated in the dotted lines, any other relevant medical information capable of electronic storage can be generated. At 78, the data generated or recorded at 72, 74, 76 can be stored on the device 22 as hospital care data or, alternatively, communicated to the database server 12 for building the relational database.

When the device 22 is used, the medical data stored on the device 22 is simply uploaded to the database 12.

The software product of the invention is configured so that suitable reports can be generated at 80 from the relational database.

A particular advantage of this approach is that the relational database contains relevant and complete information concerning the patient and the circumstances in which the patient incurred injuries or was subjected to intermediate treatment. Such a system allows for a thorough and accurate assessment of further treatment required by the patient. Furthermore, various medical operators can be associated with treatment and consultation notes.

Figure 4:
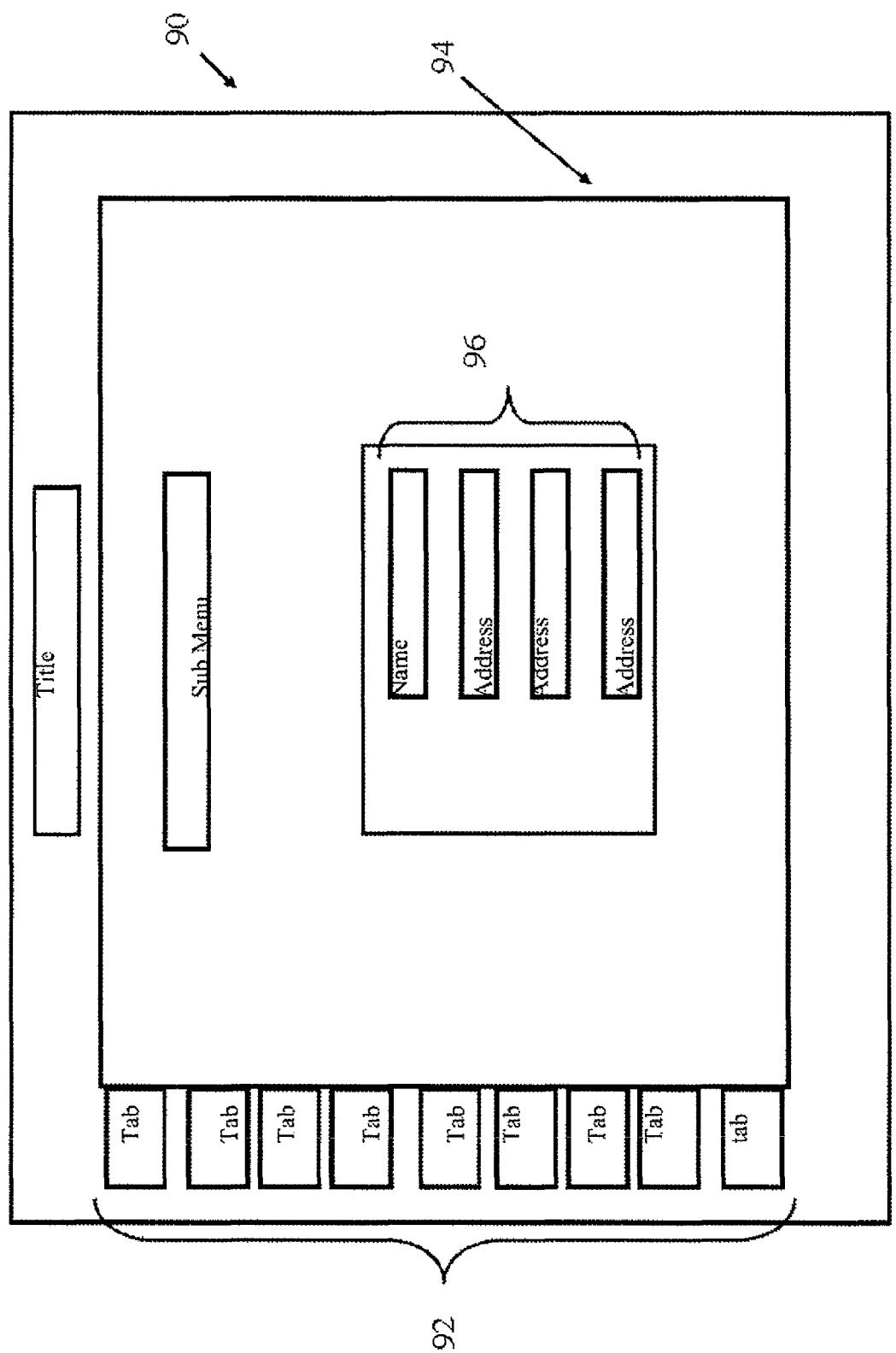
FIG. 4 shows a graphic user interface (GUI) generated by the software product for inputting patient details to a medical database.

The software product of the invention is configured so that, when executed with a data processing device, such as the laptop 18.1, a graphical user interface (GUI) 90, as shown in FIG. 4, is generated. The GUI 90 facilitates the input of relevant data required to build the medical database.

The GUI 90 includes tabs 92 for navigating between various menus. In this particular example, there is a tab 92 for each of the following forms of data entry:

a) Patient profile data
b) Capturing video data
c) The analysis of video data
d) The capture of balance data from the balance board 18.3
e) The analysis of balance data
f) Copying video data to storage device
g) Programme setup options
h) Help and demonstrations
i) Link back to a main menu.

The GUI 90 further includes a sub menu heading 94, in this case relating to patient profile capture. The GUI 90 further defines input fields 96 so that selected details of the patient can be input into various fields including name, address, city, state, zip, phone number, social security number, date of birth, sex, height, weight, and start date. The data can be manually input by the operator, or sensed data can be input from connected analytical instruments. For example, electronic scales can automatically fill in the patient's weight.

Figure 5:
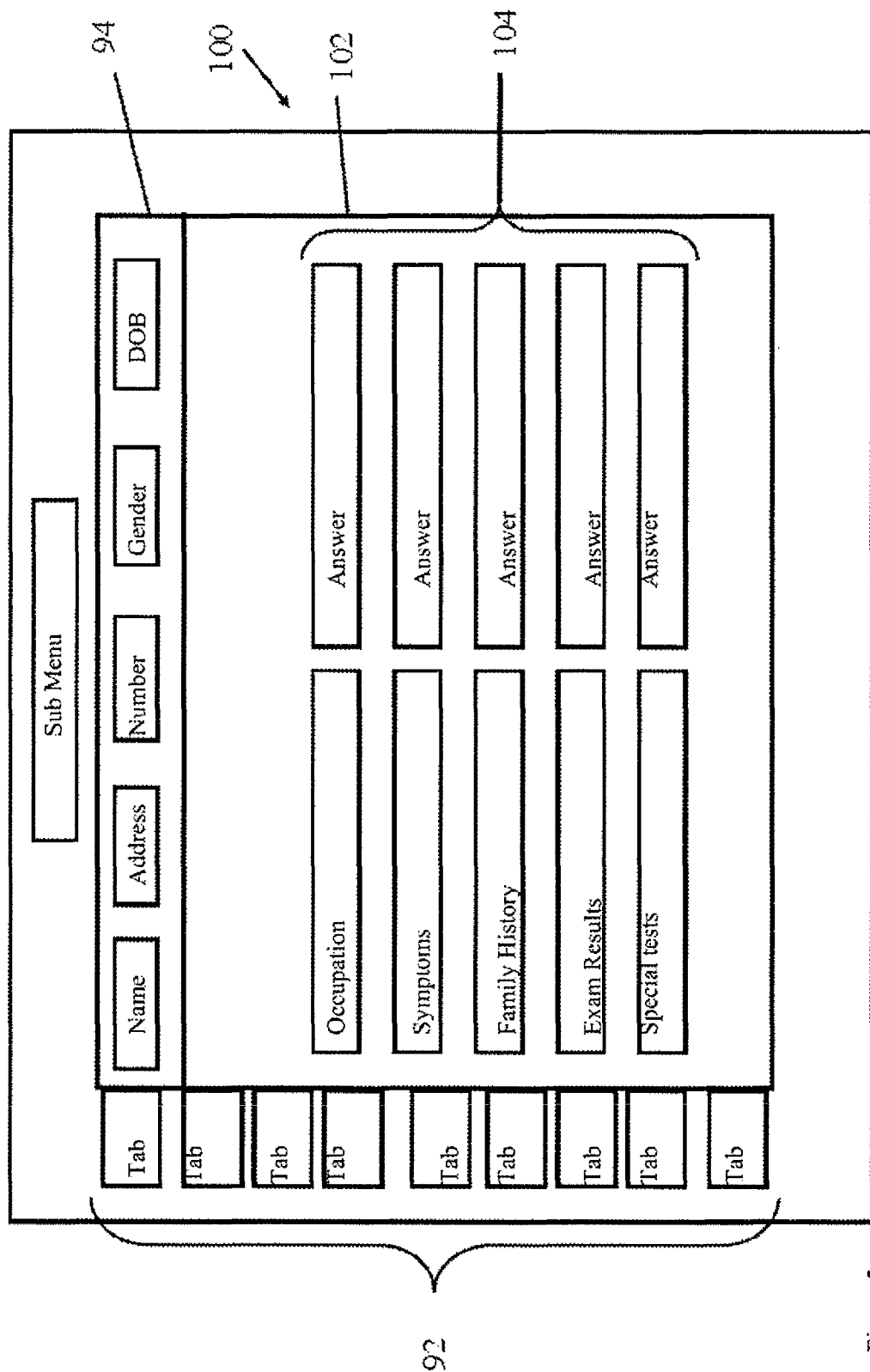
FIG. 5 shows a GUI generated by the software product for inputting further patient details to a medical database.

The software product of the invention is configured so that when the patient profile tab is executed, a GUI 100, as shown in FIG. 5, is generated.

The software product generates a patient information sub menu 102. The sub menu 102 allows selected details of the patient information to be input to the medical database via suitable fields 104. These can include such details as: Occupation, symptoms, family medical history, orthotics, prostheses/walking aids, surgery, exam results, leisure activities/sports, current medications, notes and other information, trauma and questionnaires/special tests.

Figure 6:
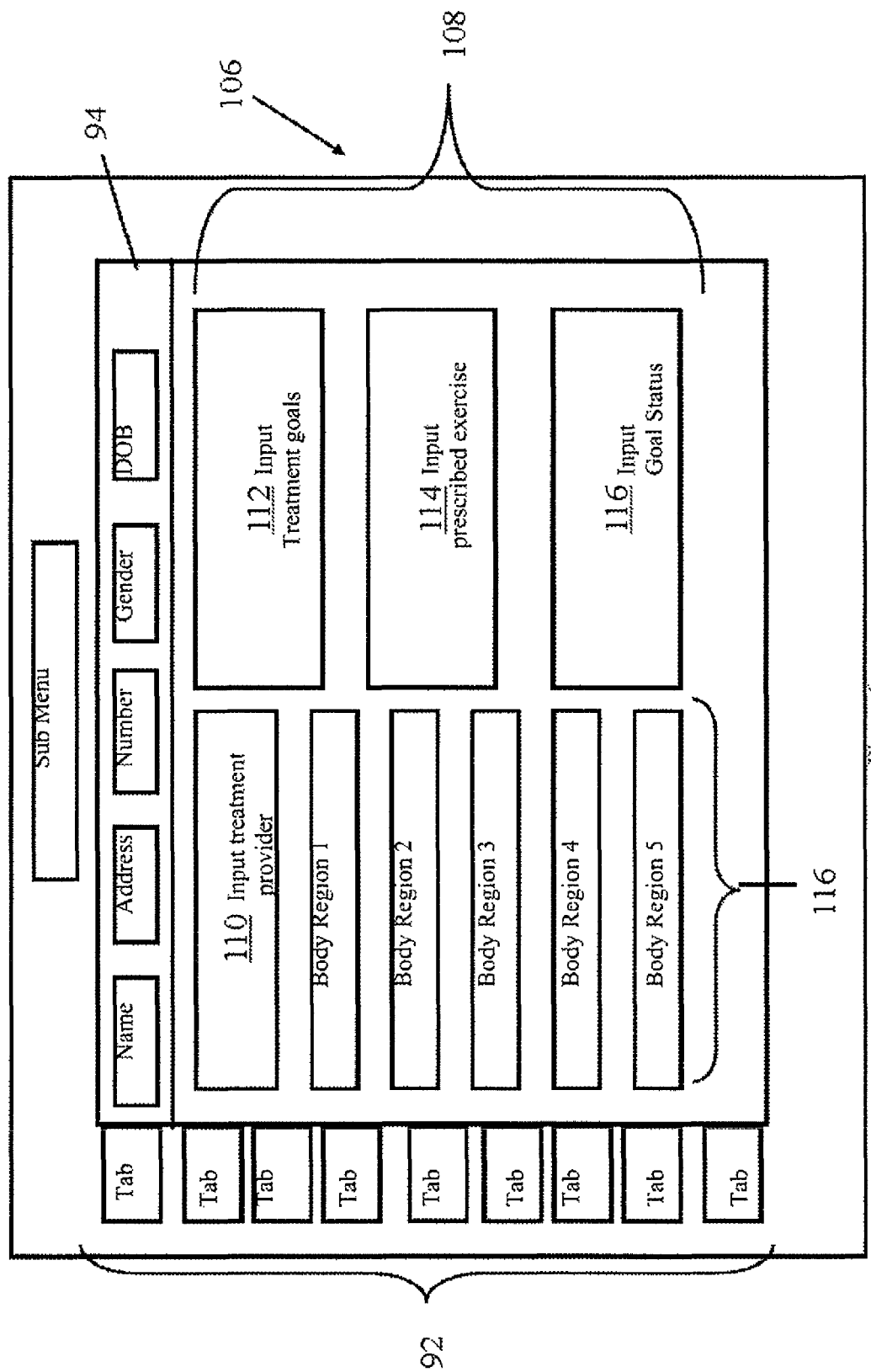
FIG. 6 shows a GUI generated by the software product for inputting treatment details to a medical database.

The software product of the invention is configured so that when a diagnostics and treatment tab is executed in the sub menu 94, a GUI 106, as shown in FIG. 6, is generated. The GUI 106 is configured so that an operator can input various diagnoses and treatment items of information in fields 108. For example, at 110, the operator can input information relating to the treatment provider. At 112, 114 and 116, the operator can input information relating to, respectively, treatment goals, prescribed exercise and goal status.

At 116, a number of fields are provided with drop down menus to permit an operator to input information relating to various body regions of the patient.

Figure 7:
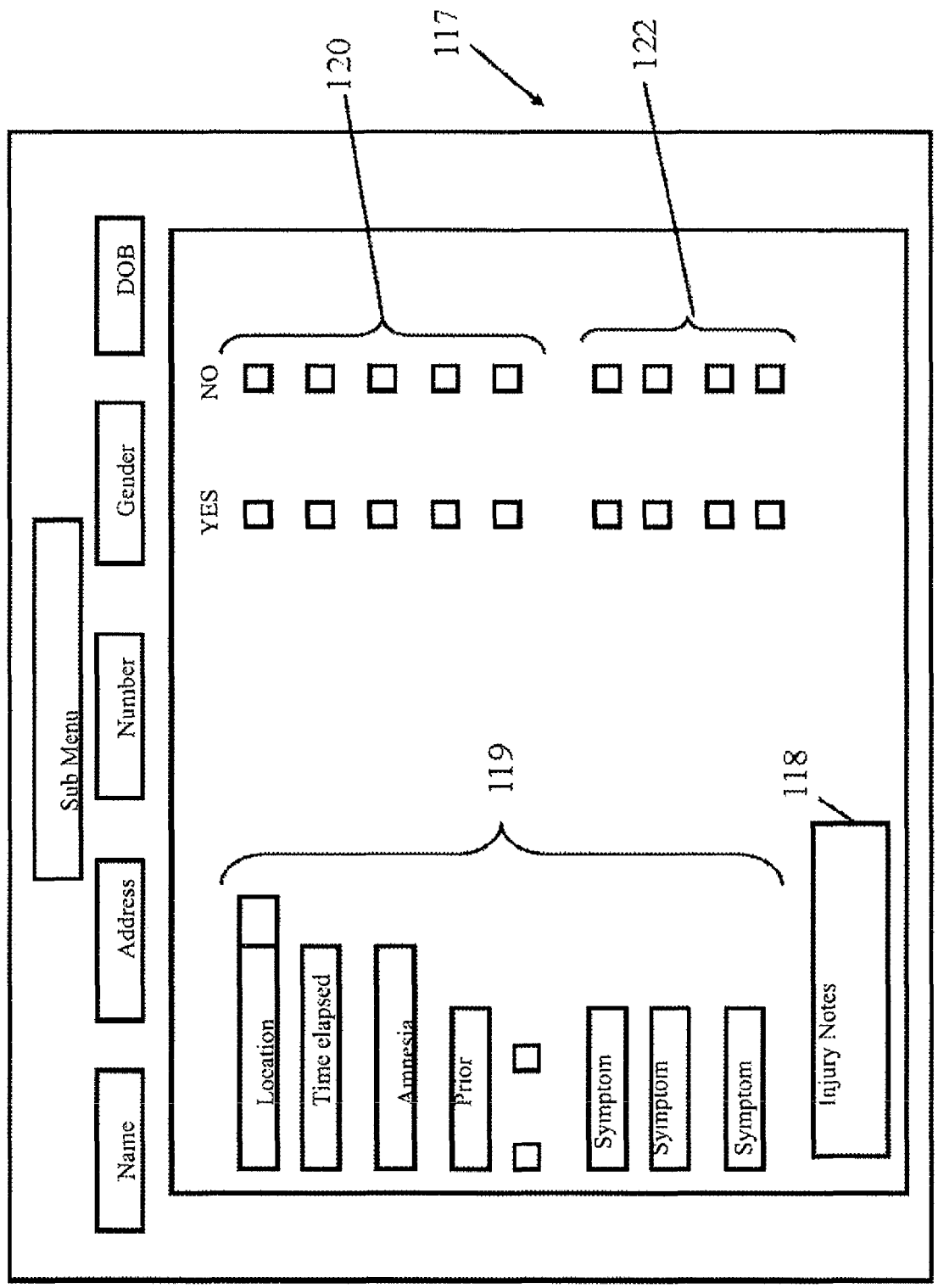
FIG. 7 shows a GUI generated by the software product for inputting diagnostic information to a medical database.

The software product of the invention is configured so that one of the tabs 92 can be executed to generate a data capture GUI 117 as shown in FIG. 7.

In this particular example, the GUI 117 would be generated in, possibly, a military application. Thus, at 119, information relating to the particular event that caused the injury can be recorded. Furthermore, the name and age of the patient can also be entered. Details of whether or not the patient has had prior blast exposure can be entered together with how much time has elapsed since the blast, and the amount of time the patient has suffered amnesia. At 118, a field is generated so that the medical operator can insert further injury notes. At 120, the software product generates a series of yes/no blocks relating to questions in connection with the patient. For example, these could include whether or not the patient suffers from headache, nausea, dizziness, hearing problems etc.

The software product is configured to generate at 122, further yes/no blocks to permit an operator to respond to pre-session exam enquiries.

Figure 8:
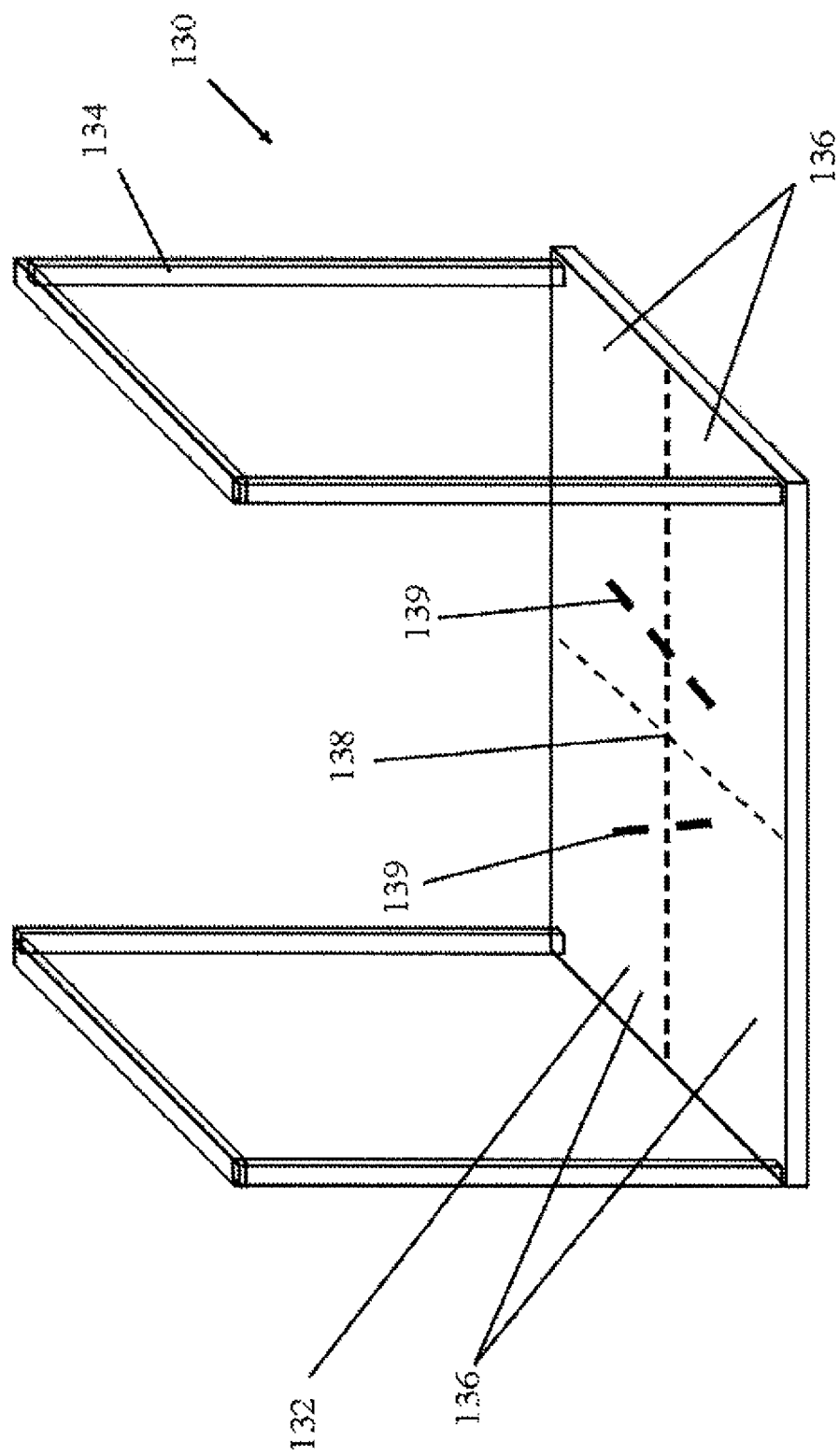
FIG. 8 shows a balance/load cell system that can provide sensor data to the medical database generated by the software product.

In FIG. 8 reference numeral 130 generally indicates a balance board or balance plate for assessing a patient's balancing ability. It will be appreciated that such an assessment is a useful indication of injury suffered by the patient and, also, the patient's general well-being.

The balance plate 130 has a plate 132 on which the patient stands and four load cells (see below) beneath the plate 132 to measure dynamic weight distribution on the plate 132 when a patient is standing on the plate 132. The balance plate 130 includes a handrail 134 for supporting the patient. The plate 132 is demarcated into four quadrants 136 and a center point 138. The four quadrants 136 and center point 138 facilitate correct positioning of a patient's feet on the plate 132. The balance plate 132 can also carry demarcations 139 to assist a patient to position his or her feet correctly.

Figure 9:
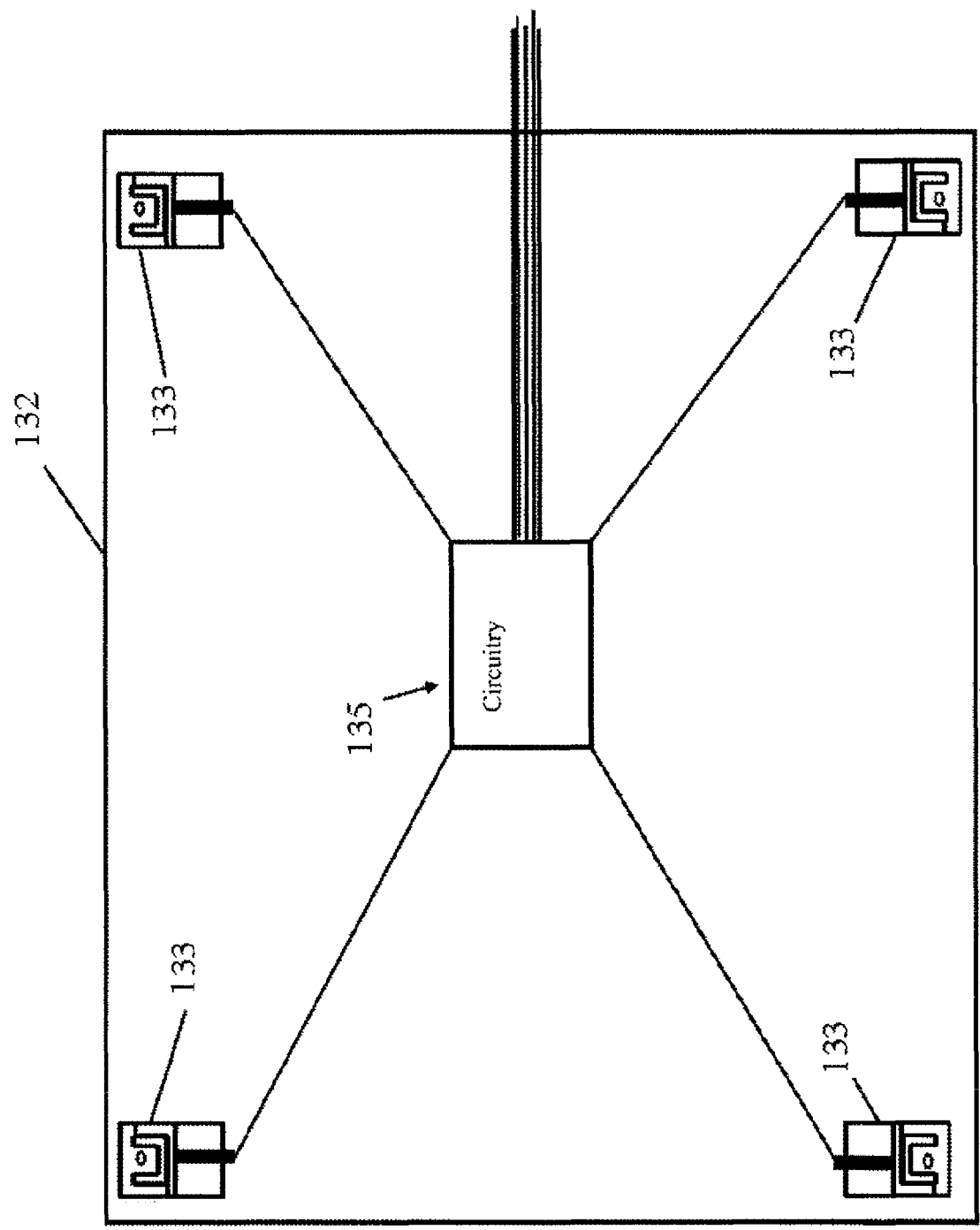
FIG. 9 shows a schematic layout of a load cell arrangement used with the system of FIG. 8 to provide balance data to the medical database generated by the product.

Further detail of the balance plate 132 is shown in FIG. 9. The balance plate 132 includes four load cells 133, each in the form of a low profile planar beam load cell. An example of such a load cell is the type PB load cell manufactured by Flintec (trade mark). Such load cells find application in compact scales, bench and floor scales and retail and counting scales. They also find application in the medical field.

In this embodiment, the load cells 133 are oriented and configured so that the balance plate defines a four-cell balance plate. As can be seen in FIG. 9, the data output from the load cells 133 is sent out with suitable circuitry 135 to be read to a processor executing an embodiment of the software product of the invention.

Figure 10:
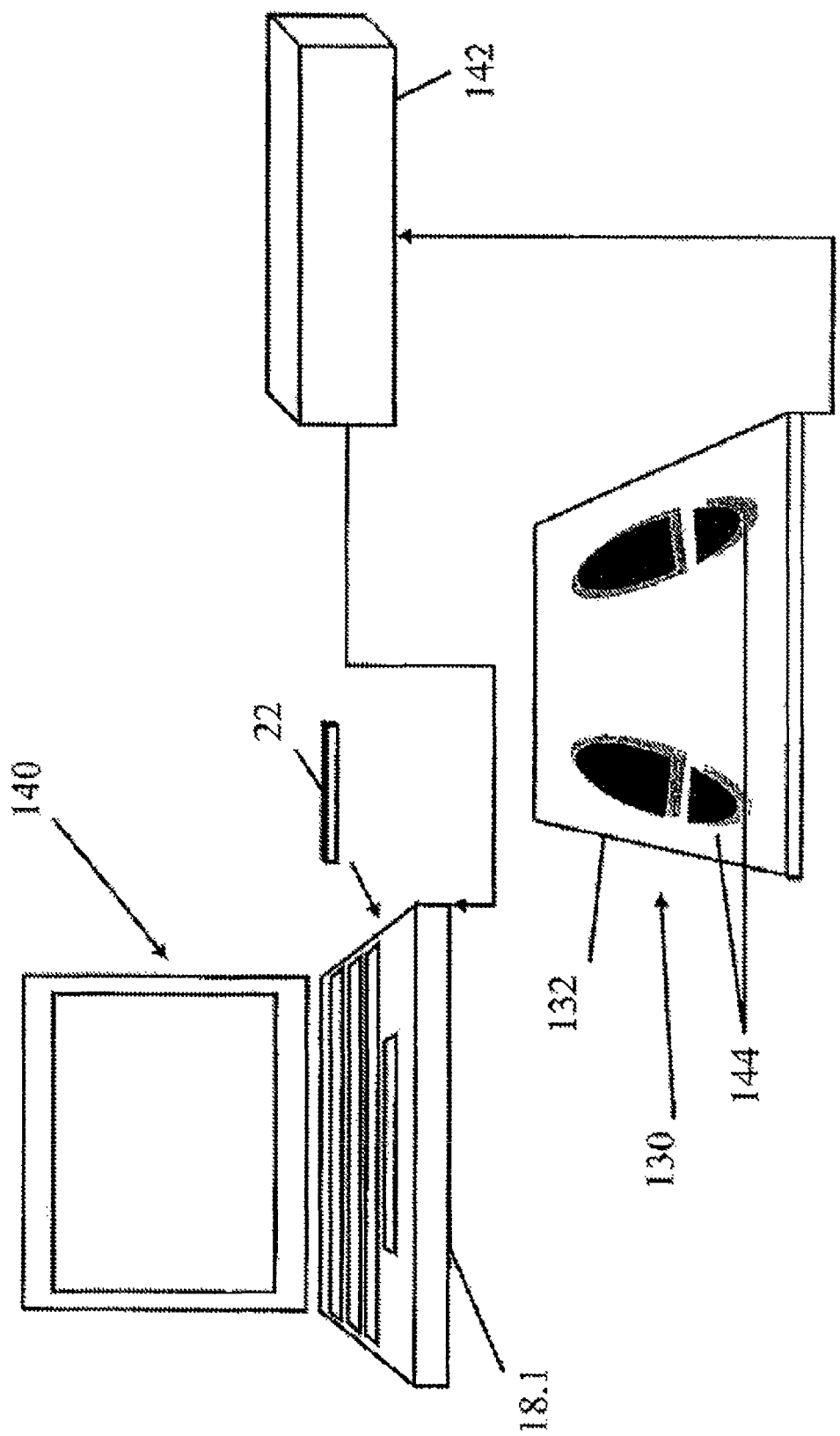
FIG. 10 shows the balance/load cell system of FIGS. 8 and 9 connected to a laptop computer programmed with the software product.

As can be seen in FIG. 10, the balance plate 130 is connected to a computer 140 with a suitable interface device 142 to facilitate communication between the plate 130 and the computer 140. In one example, the computer 140 can be the laptop 18.1 described earlier. In that case, the removable measuring device 22 is supplied with the laptop 18.1 so that data from the balance plate 130 can be stored on the device 22.

In addition or instead of the demarcated quadrants 136, the balance plate 132 can include a pair of foot positioning guides 144 to assist the patient in correctly positioning his or her feet on the balance plate 132. The purpose of the demarcated quadrants 136 or the foot positioning guides 144 or both is to ensure that a center of gravity of the patient is vertically aligned with the center point 138 when the patient is motionless.

In use, the software product of the invention is executed to generate the data capture GUI 114. The patient then stands on the balance plate 132. The patient can be stationery on the balance plate 132 or can carry out various actions depending on the type and level of analysis required.

Figure 11:
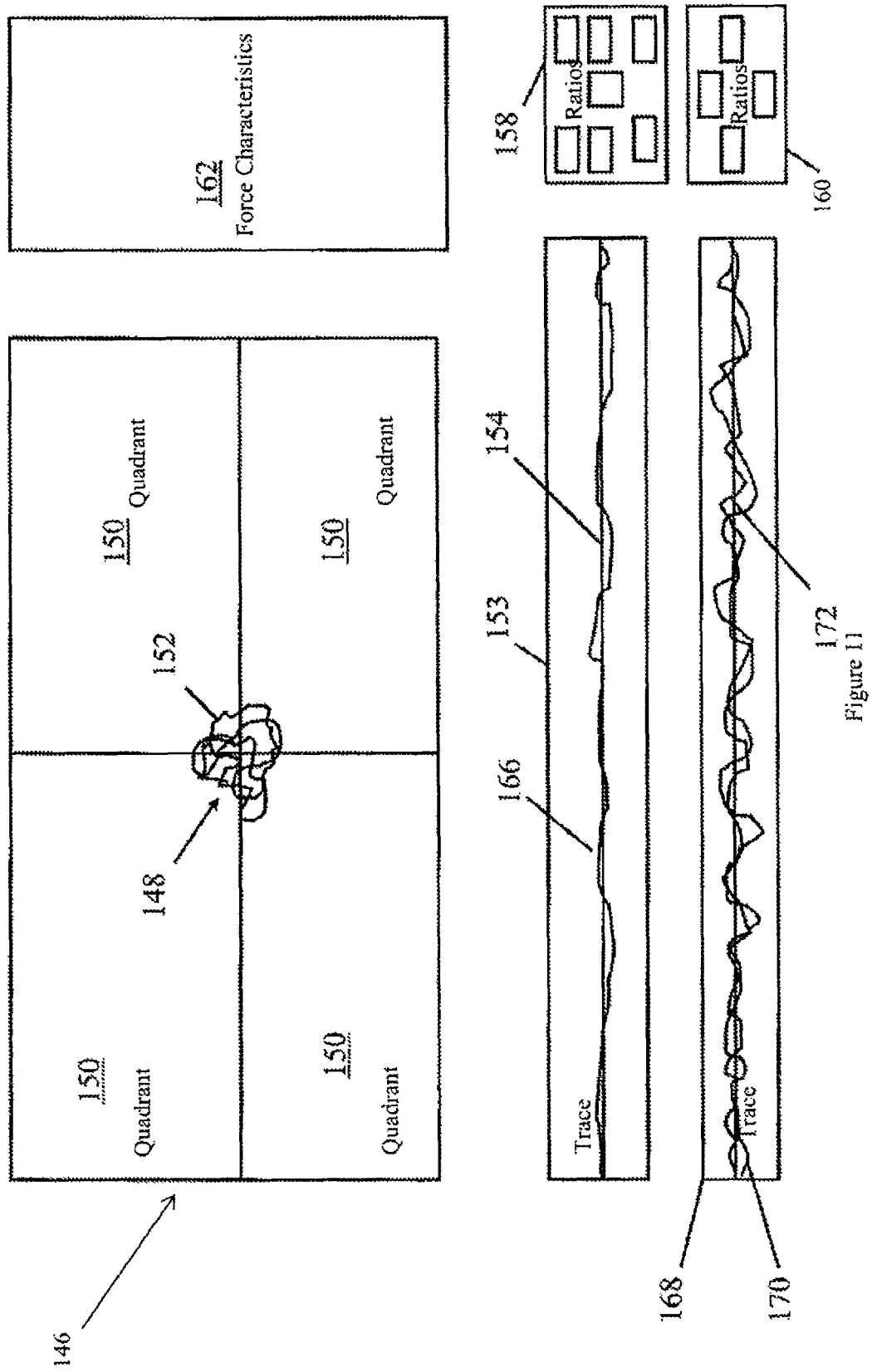
FIG. 11 shows a GUI generated by the laptop computer of FIG. 10 programmed with the software product.

The interface device 142 and the computer 140 are configured to interpret force-related data generated by the load cells 133. This data can be interpreted by the computer 140 graphically as shown in the GUI of FIG. 11.

In particular, the software product is configured so that a graphical representation of the balance plate 132 is generated as shown at 146. Thus, a center point 148 and four quadrants 150 correspond with the center point 138 and four quadrants 136 of the plate 132.

The software product is configured to generate a trace over time of a position of a center of gravity of the patient, as indicated by lines 152 on the representation 146. Thus, over a predetermined time period, an extent of variation of the center of gravity can be measured. Such data can be analyzed in a number of different ways. For example, the software product is configured to generate a representation 153 of a trace 166 indicating forwards and backwards movement of the center of gravity with respect to an axis 154. Likewise, the software product is configured to generate a representation 168 of a trace 170 indicating sideways movement with respect to an axis 172.

Furthermore, the software product, when executed, generates various quadrant ratios, shown at 158, 160. The software product can be configured so that the quadrant ratios indicate the extent of time a center of gravity of the patient is above respective quadrants. At 162, the software product generates further information relating to the characteristics of the forces detected by the load cells 133.

Figure 12:
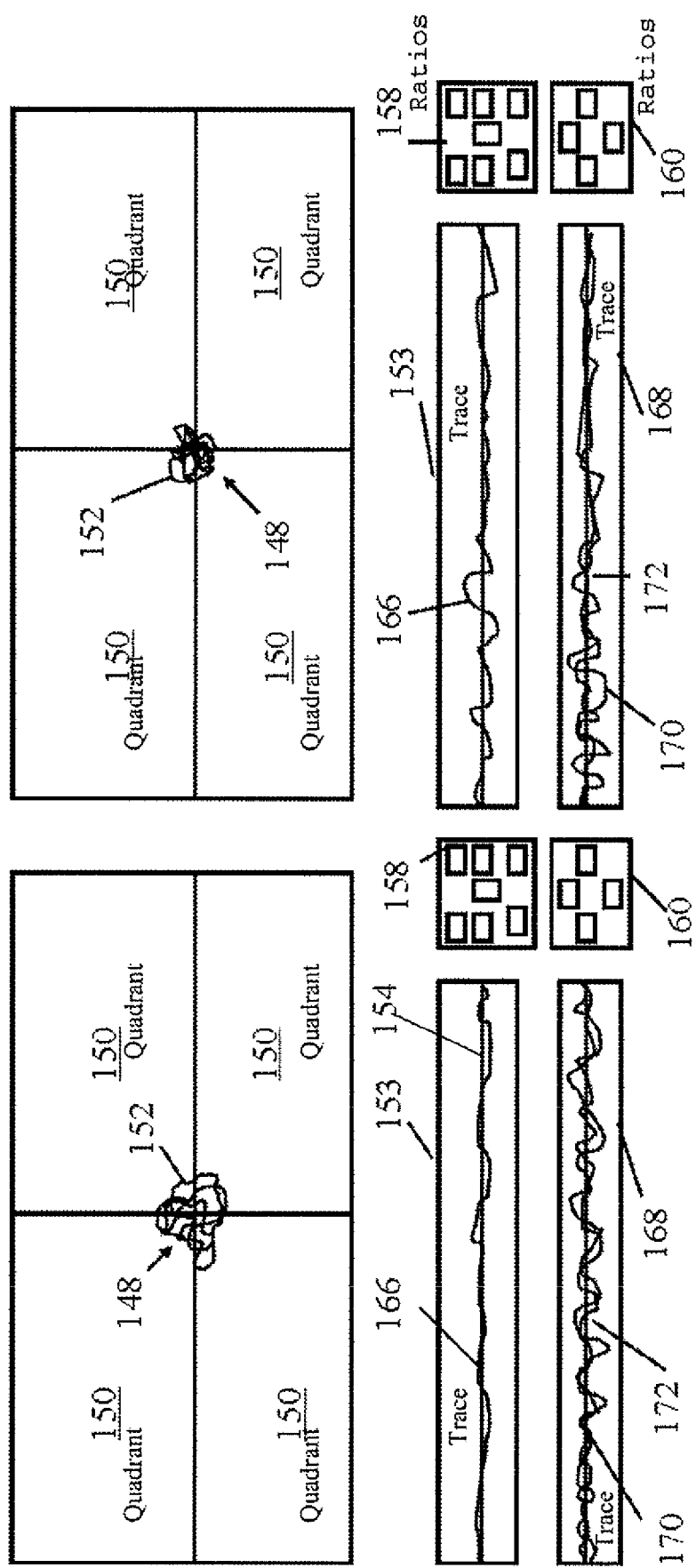
FIG. 12 shows another GUI generated by the laptop computer of FIG. 10 programmed with the software product.

In FIG. 12, there is shown a further graphical representation generated by the software product comparing two sets of data compared side by side. With reference to FIG. 10, like reference numerals refer to like parts, unless otherwise specified. In particular, the software product can be configured to record the test and replay the test for analysis and/or comparison.

Figure 13:
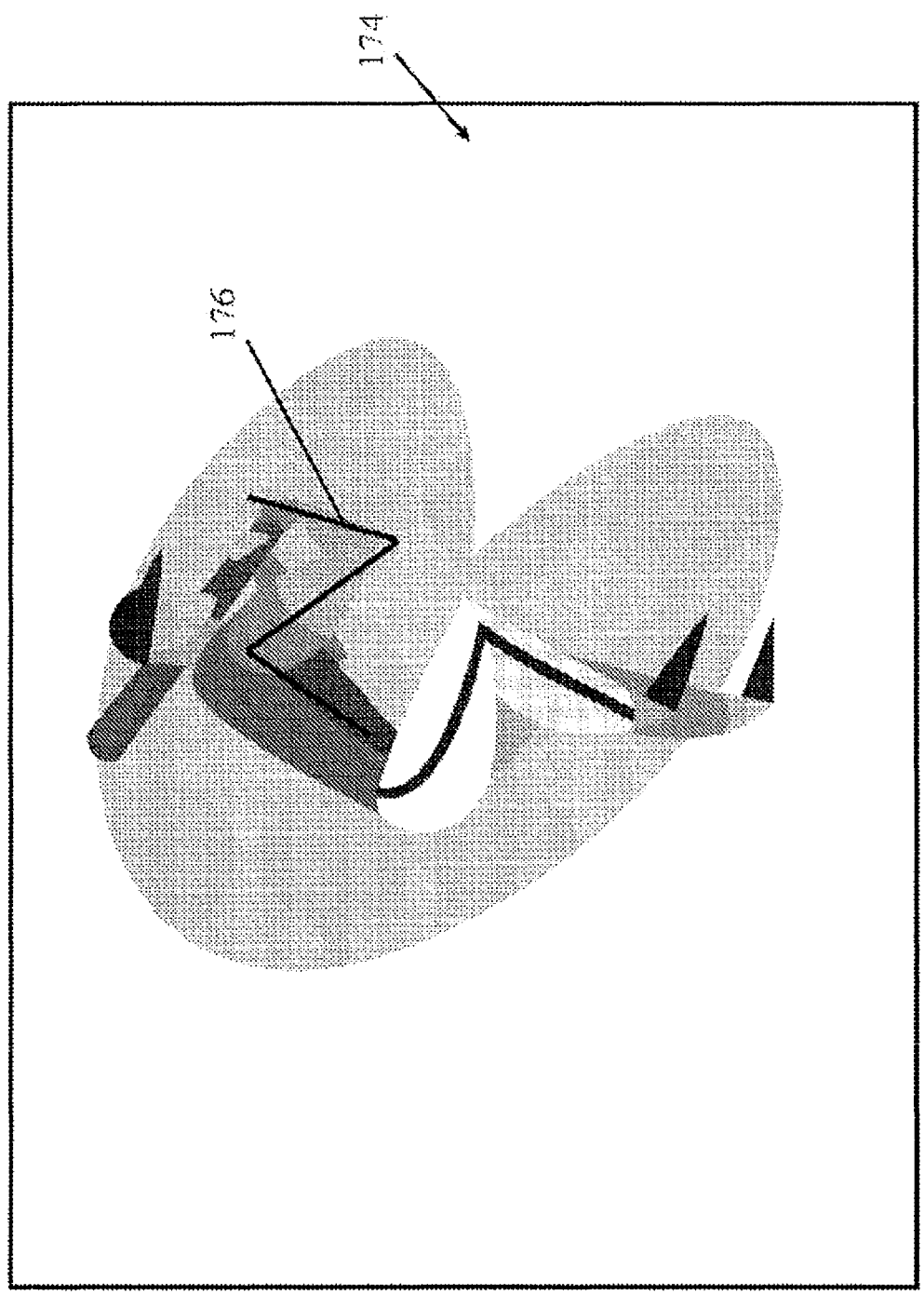
FIG. 13 shows an image generated for measuring a characteristic of a patient as a parameter to be used by the software product.
Figure 14:
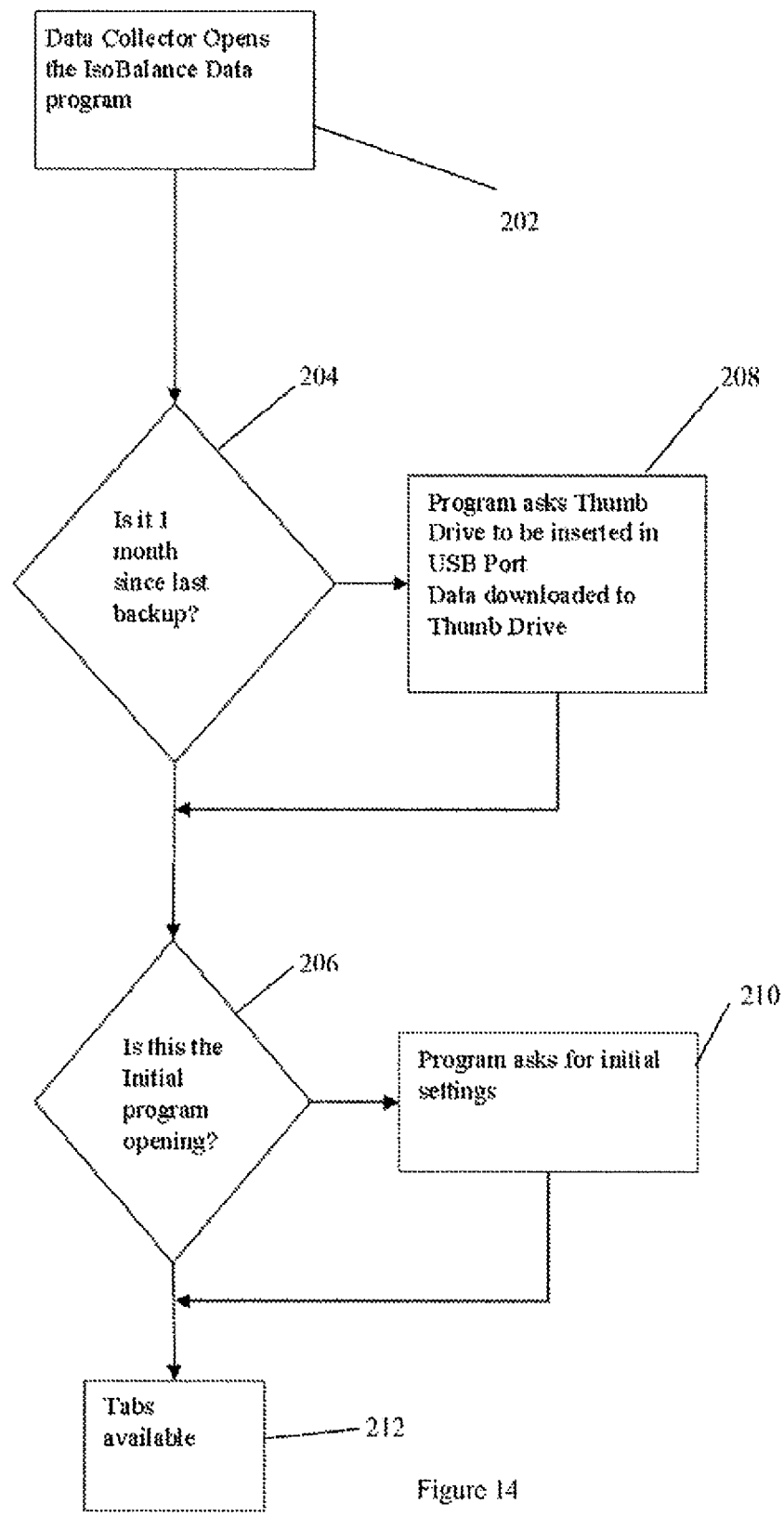
FIG. 14 shows a flowchart of the initial steps of one embodiment of a method for collecting medical data, in accordance with the invention, carried out by one embodiment of a software product, also in accordance with the invention.
Figure 15:
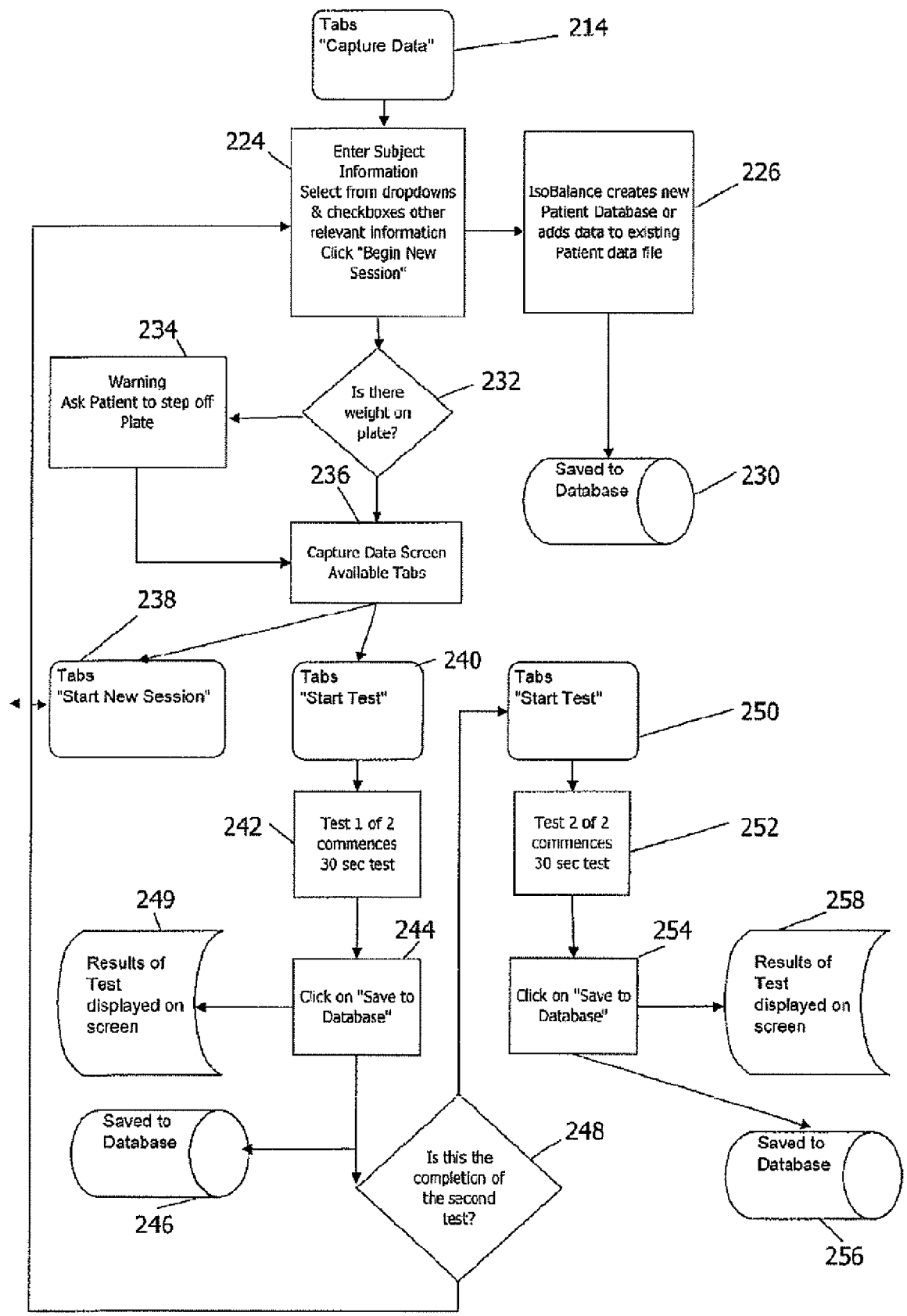
FIG. 15 shows a flowchart of steps carried out when a "Capture Data" tab generated by the software product is selected.
Figures 16, 17:
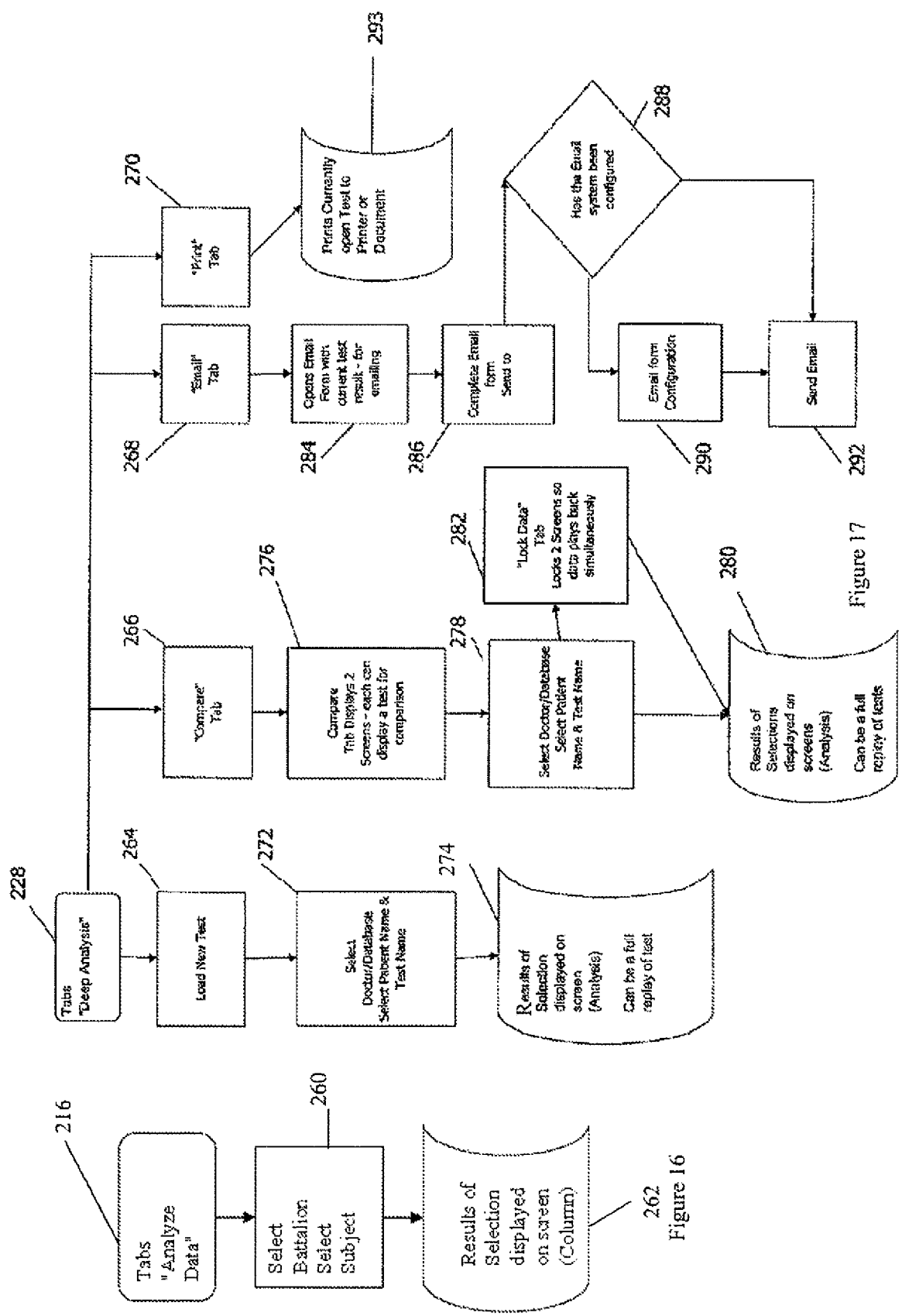
FIG. 16 shows a flowchart of steps carried out when an "Analyze Data" tab generated by the software product is selected.
FIG. 17 shows a flowchart of steps carried out when a "Deep Analysis" tab generated by the software product is selected.

In FIG. 13 reference numeral 174 is a GUI that is generated when an "Analyse Video" tab, being one of the tabs 92 is executed. In this case, the video is of a sports person performing a particular technique. The GUI 174 is generated so that the medical operator can overlie a line image 176 to determine relative angles between body parts of the patient or sportsman. By repeating the measurements at various stages of a sportsperson's treatment, the medical operator can determine the sportsperson's progress with a prescribed treatment.

In one embodiment, the software product is configured so that analysis on both the balance data and video data can be performed simultaneously. Thus, detailed information on strength, range of motion, balance and the ability of the patient to perform a range of physical and cognitive tasks can be calculated. This allows for close monitoring of a patient or sportsperson's rehabilitation.

In FIGS. 14 to 20, there are shown parts of a flowchart of one embodiment of a method, in accordance with the invention, for building a medical database which is carried out when one embodiment of a software product, in accordance with the invention, is executed. In this particular example, the method and the software product are used for building a medical database from data collected from a balance-board apparatus, of the type described above.

The method is initiated at 202 by running an embodiment of the software product, in accordance with the invention, on a suitable computational device, such as a laptop computer or PC. At 204, the software product queries whether or not a backup has been generated of the data. If the response is negative, the product enquires, at 206, whether or not the product is being executed for the first time.

If the answer to the query at 204 is positive, the software product prompts the user to run a suitable backup program at 208.

If the answer to the query at 206 is positive, the user is prompted to enter initial settings at 210. Otherwise, the software product continues to execute. At 212, the software product generates a number of tabs. These include a "Capture Data" tab at 214 (FIG. 15), an "Analyse Data" tab at 216 (FIG. 16), a "Deep Analysis" tab at 228 (FIG. 17), a "Program Setup" tab at 218 (FIG. 18), an "Exit Program" tab at 220 (FIG. 19) and a "Program Help" tab at 222 (FIG. 20).

If the user selects the Capture Data tab at 214, the user is prompted to enter subject information at 224. That can be done by selecting from dropdown menus and check boxes and also manually inputting information. At 226, the software product creates either a new patient database or adds data to an existing patient data file. That information is then saved to a database at 230. At 232 the software product enquires whether or not a weight is present on the balance plate. If the answer is positive, a warning message is generated at 234 that the patient is to step off the plate. If the result of the enquiry is negative, the software product generates a number of tabs for capturing data from the plate at 236. These include a "Start New Session" tab at 238 and a "Start Test" tab at 240.

If the user selects the Start New Session tab at 238, the software product reverts the user to step 224 so that the user can enter the patient information.

If the user selects the Start Test tab at 240, the software product initiates a first test 242 in the form of a 30 second test 242 during which the patient stands on the balance board for 30 seconds or, as envisaged above, performs any other test or is analysed in any other way. At 244, the user is prompted to save the results of the test to a database 246 and the results of the test are displayed on the screen at 249 in the manner described previously.

The product then queries whether or not the previous step was the completion of the second test at 248. If the answer to that query is positive, the product reverts to step 224. If the answer to that query is negative, the user is prompted to select the Start Test tab at 250.

At 252, the user is prompted to commence a second 30 second balance test. As before, this can be any other further test or analysis as previously discussed. At 254, the user is prompted to save the results to a database at 256. Again, at 258, the results are displayed on a screen, as previously described.

Reverting now to the block 212, if the user selects the Analyze Data tab at 216, the user is prompted to select a battalion and to select a patient or subject details at 260. At 262, the results of the selection are displayed on the screen. These would be the results of the balance test previously carried out on that particular subject.

If the user selects the Deep Analysis tab at 228, a number of options are provided. These include loading a new test at 264, selecting a "Compare" tab at 266, selecting an "Email" tab at 268 and selecting a "Print" tab at 270. If a new test is selected at 264, at 272, a doctor and database details are selected together with a selection of a patient name and a test name. At 274, the results of the selection are displayed on the screen. This can be a full replay of the test carried out on that particular patient.

If the Compare tab is selected at 266, then at 276 the software product compares two screens in the manner previously described. At 278, the user can select a doctor or a database together with a patient name and test names. This results in that selection being displayed on the screen at 280, in the manner previously described.

Alternatively, a "Lock Data" tab can be selected at 282 with the result that two screens are locked so that data can be displayed simultaneously to the user.

If the user selects the E-mail tab at 268, the software product opens an email form at 284 so that that the test results can be emailed. At 286 the completed email form is completed. At 288, the product queries whether or not the email system has been configured. If the answer to that query is negative, the software product carries out a configuration process at 290. Then, at 292, the email is sent. Alternatively, if the enquiry generates a positive result, the software product passes directly to the send email step at 292.

If the user selects the Print tab at 270, the software product generates a suitable print command signal so that a currently open test can be printed at 293.

If the user selects the Program Setup tab at 218, the product generates an enquiry as to whether or not the relevant communications port has been detected at 294. If the answer to that query is negative, the software product displays a port number at 296 and prompts the user to ensure that the plate is attached and the sensor box is turned on. If the answer to the enquiry is positive, the software product selects the communications port and the plate size at 298. Then, at 300, the software product prompts the user to select English or metric units. At 302, the user is prompted to add a new battalion to the database. At 304, the product writes the data to a system configuration file.

If the user selects the Exit Program tab at 220, the program exits at 306.

If the user selects the Program Help tab at 222, the product, at 308, generates a detailed HTML help system that is itemised with training videos, trouble shooting and set up instructions.

It will be appreciated that the software product of the invention can be of significant benefit to patients having a broad range of complaints, including neuromuscular or neurological disorders, Parkinson's disease, Traumatic Brain Injury, and/or amputees learning daily balancing tasks. It can also be beneficial in assessing fall risk in the elderly, as hip fracture after a fall puts a person at a very high risk for stroke, premature disability and ultimately death.

Figure 21:
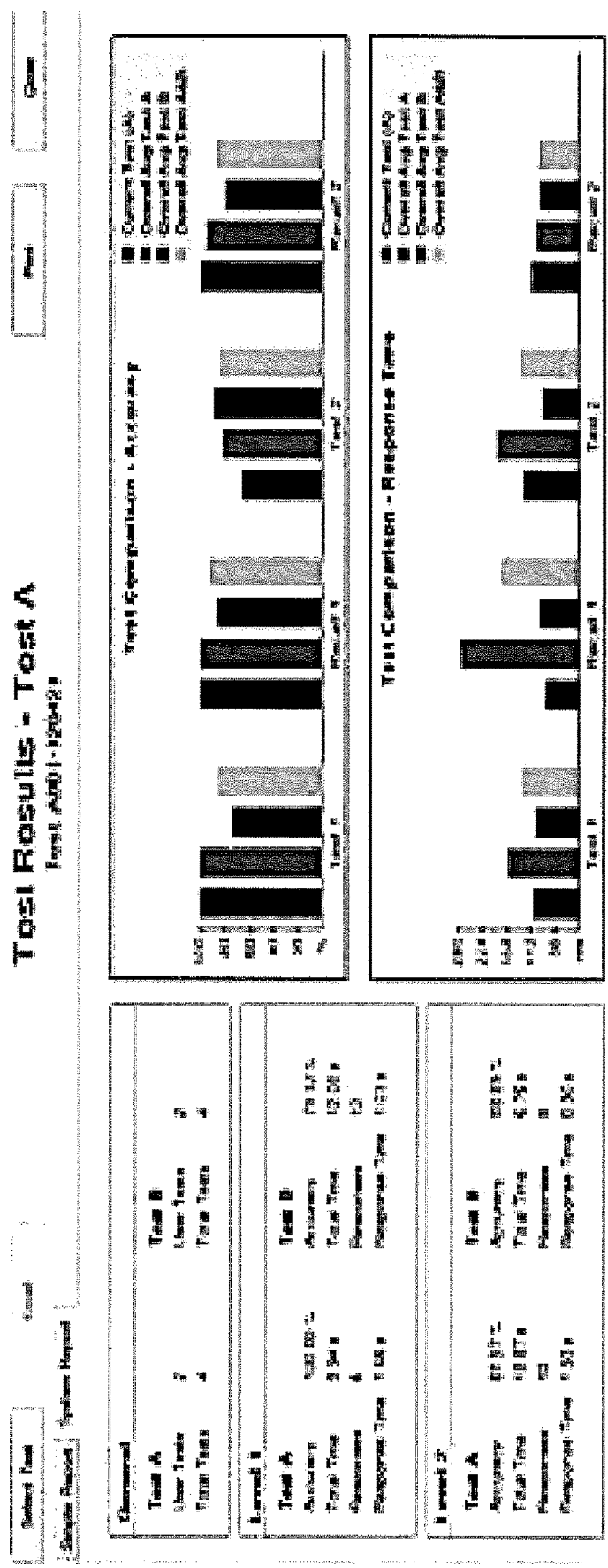
FIG. 21 is a sample result output of a computer implemented cognition assessment according to a preferred embodiment of the present invention.

One preferred form of cognition assessment is a software product, a sample of test results of which is illustrated in FIG. 21, including a set of tests designed to test the subject's ability to determine, memorize and recall the pattern of two (2) symbols. 'Arrow' keys are used on the keyboard—Right & Left—to choose the specific symbol. A preferred first task is to determine a pattern—two distinct shapes will be shown. The subject preferably uses the left or right arrow keys on a keyboard, or touches the appropriate location on the touchpad or smart-phone to make a selection. The system will display if the subject has selected the correct symbol or not. A preferred second task is to recall the set of patterns discovered in step one. The response times and selections are preferably evaluated and displayed in a graphed format and in a comparative display weighted against a database average.

Figure 22:
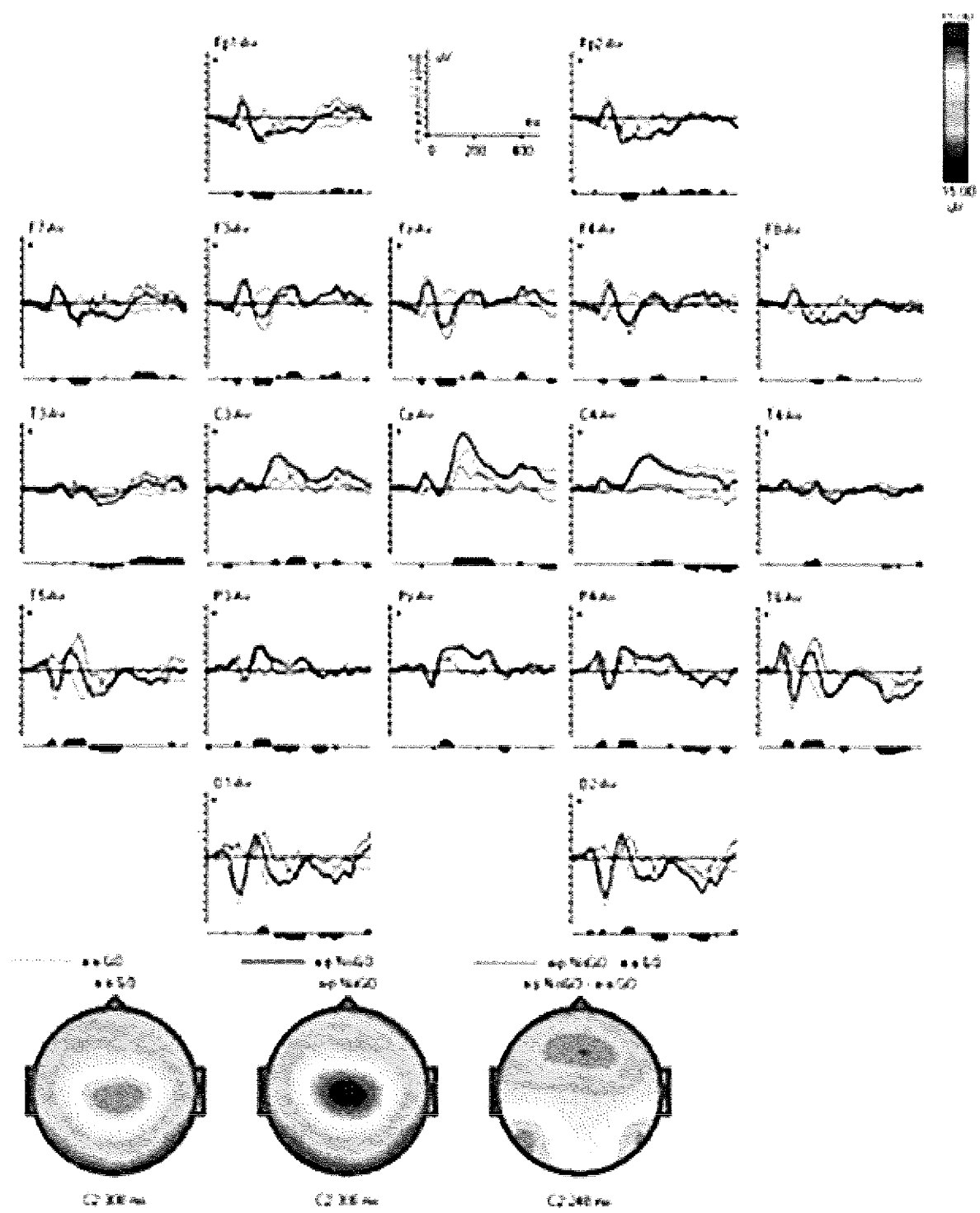
FIG. 22 is a sample result output of an event related potentials assessment according to a preferred embodiment of the present invention.

An Event Related Potentials (ERP) assessment tool, a sample of test results of which is illustrated in FIG. 22, can be used for detailed analysis of the ERP's against a normative database to detect abnormalities and map behavioural parameters and improvement. An event-related potential (ERP) is the measured brain response that is the direct result of a specific sensory, cognitive, or motor event.

More formally, it is any stereotyped electrophysiological response to a stimulus. The study of the brain in this way provides a non-invasive means of evaluating brain functioning in patients with cognitive diseases.

ERP component abnormalities in clinical research have been shown in neurological conditions such as:
Dementia
Parkinson's disease
Multiple sclerosis
Head injuries (MTBI)
Stroke An "Eye Tracking" system to measure and analyze eye movements can be incorporated in the balance system. This additional measurement would show comparative eye movements in real time with balance changes.

Figure 23:
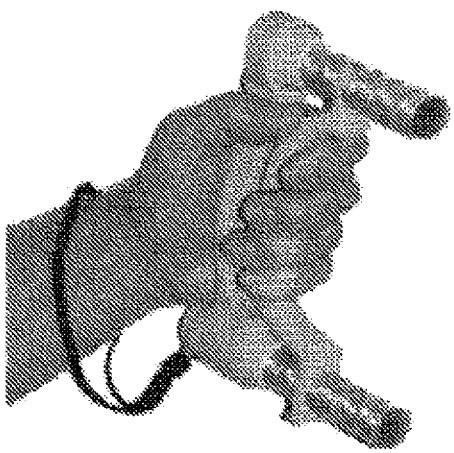
FIG. 23 is a handgrip sensor of one potential embodiment to allow initial and ongoing evaluation of fine motor controls.

A handgrip sensor such as that illustrated in FIG. 23 could be attached to the system using a USB cable or wireless/Bluetooth connection. This addition would enable the screening of grip strength and initial and ongoing evaluation of subjects with fine motor skills impairment.

A preferred construction is a strong aluminum body construction with scratch resistant UV coating. The readout preferably displays isometric grip force from 0-200 lbs. (90 kg.). The unit is typically provided with an easy-to-read LCD display that can be set to display pounds or kilograms. An integrated dynamometer also features digital load cell technology. This tool preferably allows rapid exchange testing with audible signals. The output will normally include the average, standard deviation, and coefficient of variation of a number of different tests and allows comparison with a database collection.

Figure 24:
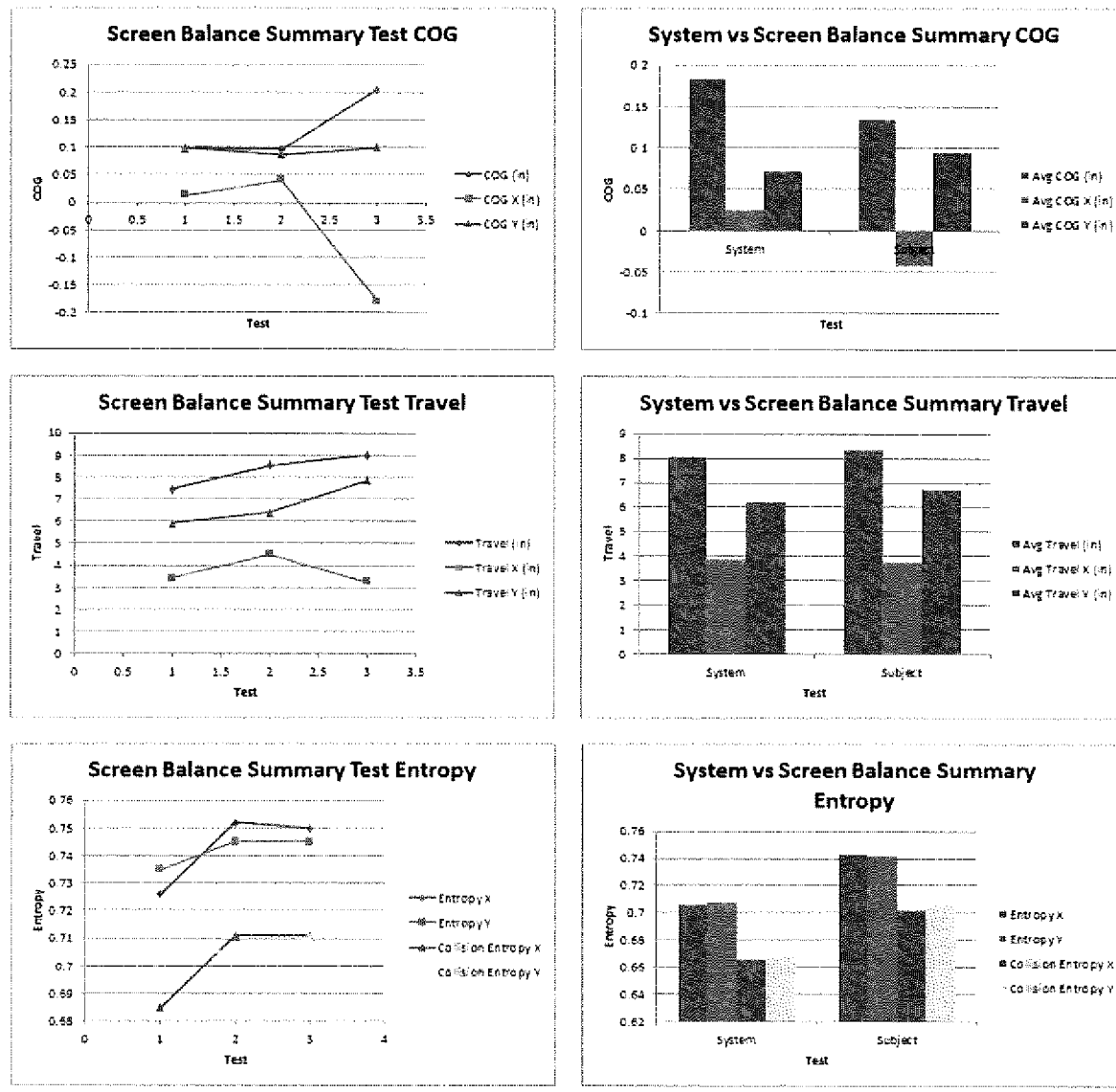
FIG. 24 is a sample result output of an entropy calculation and summary assessment according to a preferred embodiment of the present invention.

Entropy values such as those illustrated in FIG. 24 can be calculated on physiological or other data collected throughout one or more balance tests. Theoretical entropy is a measure of the order or disorder, and in this case gives an additional measure to the predictability and diversity of the test subject's activity. Preferably, both Shannon and Renyi Entropy values are produced.

Shannon entropy is static measure of entropy. Renyi entropy represents a scalable calculation based around the Shannon entropy. The Renyi entropy used in the system has been given a parameter of 2 (which represents a measure known as the "collision entropy").

Entropy calculations are typically performed using the following procedure.
1. Normalize COG data; using the mean COG point and the standard variation of that data;
2. Cluster the data into segments so the COG points overlap and produce meaningful probabilities (e.g. split the grid into 100 brackets and round the values into the nearest bracket);
3. Calculate the entropy (Shannon or Renyi);
4. Normalize the resulting entropy into the range of 0.0 to 1.0

Sway velocity can be calculated based on a subject's test results and the calculations saved and used in a pattern matching query to isolate groups or anomalous test results.

Average sway velocity is determined by calculating the sum of the COP displacements in the AP-ML plane over a trial (i.e., the sway path length) and dividing this number by the recording time, i.e., 30 seconds. The raw data for this test can be collected using the balance plate 130 illustrated in FIG. 10.

An EEG in conjunction with balance can be used as a robust clinical tool for assessment of mild traumatic brain injury (MTBI).

This system allows for a concussion assessment protocol combining a series of EEG and balance measures throughout one year post injury to document recovery of patients suffering from MTBI. This allows for an establishment of an initial baseline of subjects prior to any exposure to MTBI. A sample of the output for baseline testing is illustrated in FIG. 25 as well as the same test on the same subject, 7 days after MTBI showing the differences.

Figure 26:
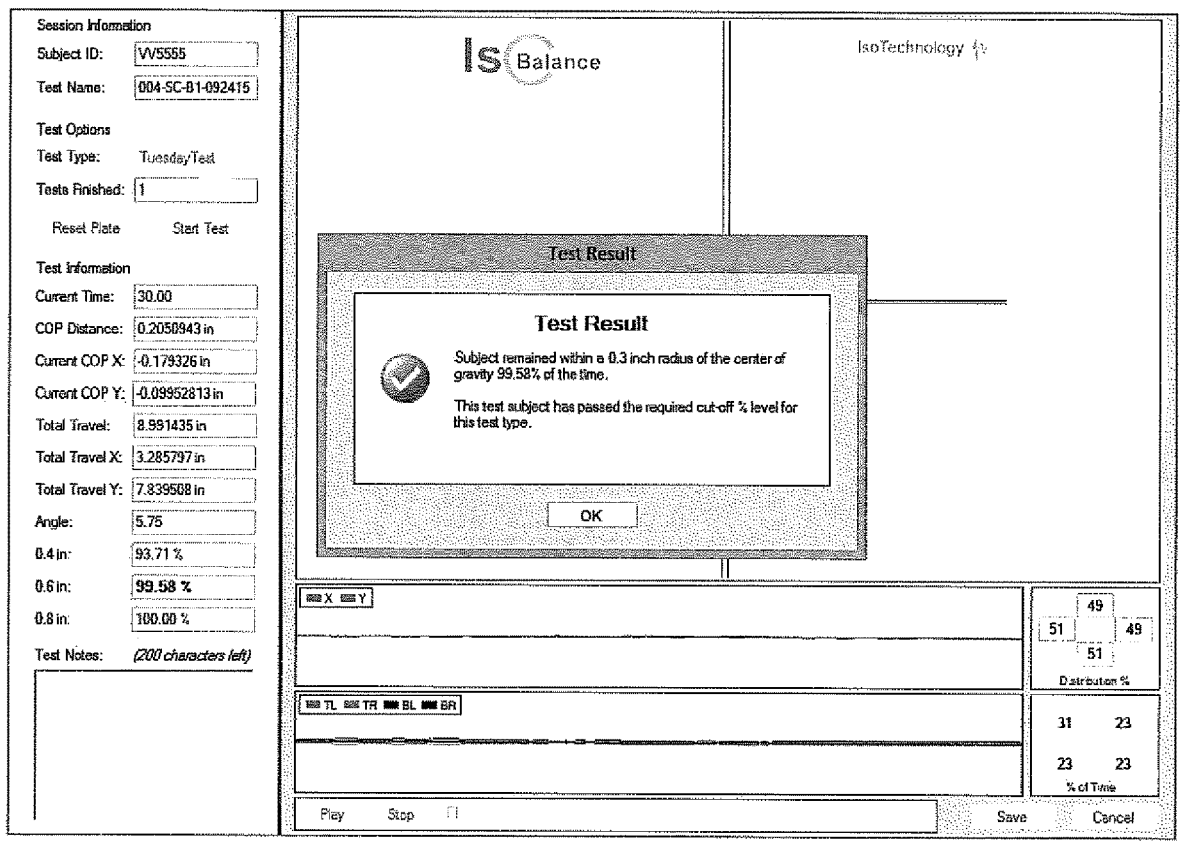
FIG. 26 is a sample output display produced using the preferred software embodiment of the present invention with alert display showing compliance with a preset parameter.

The new database system allows for the creation and editing of custom tests with durations from 30 seconds to 180 seconds. The custom tests can have different parameters and have an optional alert to indicate if the subject is within a certain parameter as illustrated in FIG. 26.

The database structure allows for all components to be modular and yet share a common database interface to allow for the easy export and import of the subject data and test results. The availability of raw and processed data from a variety of testing regimes increases the capability of the system to provide an accurate and comprehensive set of indicators relating to a subject's physical condition.

The cumulative database can be compiled individually in any one system, shared using the export function, or imported and used for comparative analysis of subject tests.

The addition of the balance sway velocity calculation will allow for advanced grouping of subject test results within the database and assist in detecting outliers and anomalous tests.

It is to be understood that the terminology employed above is for the purpose of description and should not be regarded as limiting. The described embodiments are intended to be illustrative of the invention, without limiting the scope thereof The invention is capable of being practised with various modifications and additions as will readily occur to those skilled in the art.

Throughout the specification, including the claims, where the context permits, the term "comprising" and variants thereof such as "comprises" or "comprising" are to be interpreted as including the state of integer or integers without necessarily excluding any other integers.

The invention claimed is:

1. A system for assessing a patient's balancing ability in order to facilitate ascertaining the patient's current physiological condition, the system comprising:
a balance plate for measuring Center of Gravity (COG) dynamic weight distribution data of the patient while standing, the balance plate including at least one load cell;
a handgrip sensor independent of the balance plate for measuring grip strength data of the patient contemporaneously with measuring the COG dynamic weight distribution data of the patient;
a video data collection device for capturing video of the patient performing a cognitive task contemporaneously with measuring the COG dynamic weight distribution data and the grip strength data;
a local processor in operative communication with the balance plate, the handgrip sensor, and the video data collection device, the local processor being configured to generate data pertaining to the patient's physiological condition from the grip strength data and the dynamic weight distribution data and generate data pertaining to the ability of the patient to perform the cognitive task in combination with the COG dynamic weight distribution data generated by the balance plate; and
an electronic database configured to receive the COG dynamic weight distribution data, the grip strength data, and the data pertaining to the ability of the patient to perform the cognitive task from the local processor, the electronic database being accessible over a communication network.

2. The system of claim 1, further comprising a removable memory storage device configured to store the patient's data from the local processor for delivery to the electronic database.

3. The system of claim 2, wherein the removable memory storage device is a USB flash drive.

4. The system of claim 1, wherein the local processor is a laptop computer.

5. The system of claim 1, wherein the balance plate includes four load cells.

6. The system of claim 1, wherein the balance plate is configured to measure an extent of variation of the center of gravity of the patient over a predetermined time period.

7. The system of claim 6, wherein the predetermined time period is at least 30 seconds.

8. The system of claim 1, wherein the local processor is configured to generate a trace over time of a position of a center of gravity of the patient.

9. The system of claim 1, wherein the electronic database is accessible over the Internet.

10. The system of claim 1, wherein the cognitive task includes memory recall of a pattern of at least two symbols.

11. The system of claim 1, wherein the handgrip sensor is in wireless communication with the local processor.

12. The system of claim 1, wherein the handgrip sensor is operably connected to the local processor via a Bluetooth connection.

13. The system of claim 1, wherein the handgrip sensor includes a dynamometer.

14. The system of claim 1, wherein the local processor is configured to calculate entropy values based on the data collected from the balance plate.

15. The system of claim 1, wherein the local processor is configured to calculate Shannon entropy values based on the data collected from the balance plate.

16. The system of claim 1, wherein the local processor is configured to calculate Shannon entropy values and Renyi entropy values based on the data collected from the balance plate.

17. A system for assessing a patient's balancing ability in order to facilitate ascertaining the patient's current medical status, the system comprising:
- a balance plate for measuring Center of Gravity (COG) dynamic weight distribution data of the patient while standing, the balance plate including at least one load cell;
- at least one sensor independent of the balance plate for measuring a fine motor skill data of the patient contemporaneously with measuring the COG dynamic weight distribution data of the patient;
- a video data collection device for capturing video of the patient performing a cognitive task contemporaneously with measuring the COG dynamic weight distribution data and the fine motor skill data;
- a local processor in operative communication with the balance plate, the at least one sensor, and the video data collection device, the local processor being configured to generate data pertaining to the patient's fine motor skills based on the fine motor skill data generated by the at least one sensor, generate balance data based on the COG dynamic weight distribution data, and generate data pertaining to the ability of the patient to perform the cognitive task in combination with the COG dynamic weight distribution data generated by the balance plate; and
- an electronic database configured to receive the COG dynamic weight distribution data, the fine motor skill data from the local processor, and the data pertaining to the ability of the patient to perform the cognitive task, the electronic database being accessible over a communications network.

18. The system of claim 17, wherein the at least one sensor for measuring the fine motor skill data of the patient includes a handgrip sensor for measuring handgrip strength data of the patient.

19. The system of claim 17, wherein the at least one sensor for measuring the fine motor skill data of the patient includes an eye tracking sensor for measuring eye movement data of the patient.

20. A method for assessing a patient's balancing ability in order to facilitate ascertaining the patient's current medical status, the method comprising:
- measuring an extent of variation of the patient's center of gravity (COG) while standing with a balance plate over a predetermined period of time to generate dynamic weight distribution data;
- measuring fine motor skill data of the patient with at least one sensor, wherein the at least one sensor is independent of the balance plate and the measuring of the fine motor skill data occurs contemporaneously with the measuring of the patient's COG;
- capturing video of the patient performing a cognitive task contemporaneously with the measuring of the patient's COG;
- analyzing, with a processor, the patient's dynamic weight distribution data to determine the patient's balancing ability;
- analyzing, with the processor, the patient's fine motor skill data to determine the patient's fine motor skills;
- analyzing, with the processor, the patient's ability to perform the cognitive task in combination with the patient's dynamic weight distribution data generated by the balance plate; and
- ascertaining the patient's medical status using the patient's balancing ability, the patient's fine motor skills, and the patient's ability to perform the cognitive task.

21. The method of claim 20, wherein the fine motor skill data is measured by a handgrip sensor for measuring handgrip strength data of the patient.

22. The method of claim 20, wherein the fine motor skill data is measured by an eye tracking sensor for measuring eye movement data of the patient.

* * * * *